(12) United States Patent
Zechiedrich et al.

(10) Patent No.: US 8,460,924 B2
(45) Date of Patent: Jun. 11, 2013

(54) SUPERCOILED MINIVECTORS™ FOR GENE THERAPY APPLICATIONS

(75) Inventors: E. Lynn Zechiedrich, Houston, TX (US); Jonathan Fogg, Houston, TX (US); Daniel James Catanese, Jr., Houston, TX (US); Erol Bakkalbasi, Houston, TX (US); Brian E. Gilbert, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 12/905,612

(22) Filed: Oct. 15, 2010

(65) Prior Publication Data

US 2011/0160284 A1 Jun. 30, 2011

Related U.S. Application Data

(60) Provisional application No. 61/252,455, filed on Oct. 16, 2009.

(51) Int. Cl.
*C12N 15/63* (2006.01)
*C12N 15/85* (2006.01)
*C07H 21/02* (2006.01)
*C07H 21/04* (2006.01)

(52) U.S. Cl.
USPC ............ 435/320.1; 536/23.1; 536/24.31; 536/24.33; 536/24.5; 435/325

(58) Field of Classification Search
None
See application file for complete search history.

(56) References Cited

U.S. PATENT DOCUMENTS

| | | | |
|---|---|---|---|
| 5,212,087 A * | 5/1993 | Fournier et al. ............ | 435/254.2 |
| 6,964,861 B1 | 11/2005 | Gerard et al. | |
| 7,622,252 B2 | 11/2009 | Zechiedrich et al. | |
| 2006/0211117 A1 | 9/2006 | Bigger et al. | |
| 2008/0279870 A1 | 11/2008 | Inghirami et al. | |
| 2009/0123467 A1 | 5/2009 | Bedi et al. | |

FOREIGN PATENT DOCUMENTS

| WO | WO 94/09127 A2 | 4/1994 |
|---|---|---|
| WO | WO 02/46372 A1 | 6/2002 |
| WO | WO 02/083889 A2 | 10/2002 |
| WO | WO 03/064623 A2 | 8/2003 |
| WO | WO 03/103600 A2 | 12/2003 |

OTHER PUBLICATIONS

Scherr et al. (Cell Cycle 2:3, 251-257, 2003).*
Andersen, A. et al., "Strand specificity of the topoisomerase II mediated double-stranded DNA cleavage reaction," *Biochemistry*, 28(15):6237-44 (1989).
Bliska, J. and Cozzarelli, N., "Use of Site-specific Recombination as a Probe of DNA Structure and Metabolism in Vivo," *J. Mol. Biol.*, 194:205-218 (1987).
Brown, P.O. and N.R. Cozzarelli, "A Sign Inversion Mechanism for Enzymatic Supercoiling of DNA," *Science* 206:1081-1083 (1979).
Corbett, A. et al., "A Two-Site Model for Enzyme-Mediated DNA Cleavage," *J. Biol.Chem.*, 267(2):683-686 (1992).
Déclais, A. et al., "The complex between a four-way DNA junction and T7 endonuclease I," *The EMBO Journal*, 22(6):1398-1409 (2003).
Fogg, J. et al., "Yeast resolving enzyme CCE1 makes sequential cleavages in DNA junctions within the lifetime of the complex," *Biochemistry*, 39(14):4082-9 (2000).
Fogg, J. et al., "Sequence and functional-group specificity for cleavage of DNA junctions by RuvC of *Escherichia coli*," Biochemistry, 38(35):11349-58 (1999).
Hamiche, A. and Prunell, A., "Chromatin reconstitution on small DNA rings. V. DNA thermal flexibility of single nucleosomes," *J. Mol. Biol.*, 228(2):327-37 (1992).
Hiller, D. et al., "Simultaneous DNA binding and bending by EcoRV endonuclease observed by real-time fluorescence," *Biochemistry*, 42(49):14375-85 (2003).
Khodursky, A. et al., "Topoisomerase IV is a target of quinolones in *Escherichia coli*," *Proc. Natl. Acad. Sci. USA*, 92, pp. 11801-11805 (1995).
Kvaratskhelia, M. et al., "Holliday Junction Resolution is Modulated by Archaeal Chromatin Components in Vitro," *J. Biol. Chem.*, 277(4):2992-2996 (2002).
Liu, Z. et al., "Topological information embodied in local juxtaposition geometry provides a statistical mechanical basis for unknotting by type-2 DNA topoisomerases," *J. Mol. Biol.*, 361(2):268-85 (2006).
Liu, Z. et al., "Inferring global topology from local juxtaposition geometry: interlinking polymer rights and ramifications for topoisomerase action," *Biophys J.*, 90(7):2344-55 (2006).
Lopez, C. et al., "A role for topoisomerase III in a recombination pathway alternative to RuvABC," *Mol. Microbiol.*, 58(1):80-101 (2005).
Osheroff, N., "Effect of antineoplastic agents on the DNA cleavage/religation reaction of eukaryotic topoisomerase II: inhibition of DNA religation by etoposide," *Biochemistry*, 28(15):6157-60 (1989).
Stasiak, A., et al., "Electrophoretic Mobility of DNA Knots," *Nature*, 384:122 (1996).
Tolmachov, O. et al., "RecET driven chromosomal gene targeting to generate a RecA deficient *Escherichia coli* strain for Cre mediated production of minicircle DNA," *BMC Biotechnol.*, 6:17 (2006).
Vayssc, L. et al., "Nuclear-targeted minicircle to enhance gene transfer with non-viral vectors in vitro and in vivo," *J. Gene Med.*, 8(6):754-63.
Wasserman, S.A. and N.R. Cozzarelli, "Biochemical Topology: Applications to DNA Recombination and Replication," *Science*, 232:951-960 (1986).
Zechiedrich, E. et al., "Double-stranded DNA cleavage/religation reaction of eukaryotic topoisomerase II: evidence for a nicked DNA intermediate," *Biochemistry*, 28(15):6229-36 (1989).

(Continued)

*Primary Examiner* — Amy Bowman
(74) *Attorney, Agent, or Firm* — Winstead PC

(57) ABSTRACT

The present invention relates to nucleic acid molecule compositions comprising MiniVectors™ encoding a nucleic acid sequence and methods of gene therapy using MiniVectors encoding a nucleic acid sequence.

7 Claims, 10 Drawing Sheets

OTHER PUBLICATIONS

Zechiedrich, E. et al., "Roles of topoisomerases in maintaining steady-state DNA supercoiling in *Escherichia coli*," *J. Biol. Chem.*, 275(11):8103-13 (2000).

Zechiedrich, E. et al., "Topoisomerase IV, not gyrase, decatenates products of site-specific recombination in *Escherichia coli*," *Genes & Development*, 11:2580-2592 (1997).

Bates, A.D. and Maxwell, A., "DNA Topology," Oxford University Press:NY, pp. 25-31, 38-39, 107-115 (2005).

Burnier, Y. et al., "DNA Supercoiling Inhibits DNA Knotting," *Nucleic Acids Research*, 36(15):4956-4963 (2008).

Lewin, B., "Genes VI," Oxford University Press: NY, pp. 109-112 & 550-554 (1997).

Deibler, R.W., et al., "Topoisomerase IV, Alone, Unknots DNA in *E. coli*," *Genes and Development*, 15(6): 748-761 (2001).

Darquet, A.M., et al., "Minicircle: An Improved DNA Molecule for In Vitro and In Vivo Gene Transfer," *Gene Therapy*, 6: 209-218 (1999).

Napoli, A., et al., "A Novel Member of the Bacterial-Archeal Regular Family is a Nonspecific DNA Binding-Protein and Induces Positive Supercoiling," *J. Biol. Chem.*, 276(14): 10745-10752 (2001).

Adams, et al., "The Role of Topoisomerase IV in Paritioning Bacterial Replicons and the Structure of Catenated Intermediates in DNA Replication," *Cell*, 71: 277-288 (1992).

Zhao, N. et al., "Transfection of shRNA-Encoding Minivector DNA of a Few Hundred Base Pairs to Regulate Gene Expression in Lymphoma Cells," *Gene Therapy*: 1-5 (2010).

Hu, S., et al., "MicroRNA-210 as a Novel Therapy for Treatment of Ischemic Heart Disease," *J. Am. Heart Dis.*, S124-S131: 122 (11) Suppl. 1 (2010).

Fogg, J. M., et al., "Exploring Writhe in Supercoiled Minicircle DNA," *J. Phys.: Condens. Matter*, 18: S145-S159 (2006).

International Search Report and Written Opinion from International Application No. PCT/US2010/052920 filed on Oct. 15, 2010, date of mailing: Jul. 12, 2011.

* cited by examiner

Fig. 1 Preparation of minivector encoding shRNA for gene silencing

Fig. 2 High cell transfection/gene silencing capacity of the MiniVectors in the hard-to-transfect lymphoma cells Fig. 3 The minivector-induced ALK gene silencing and growth arrest of ALCL cells

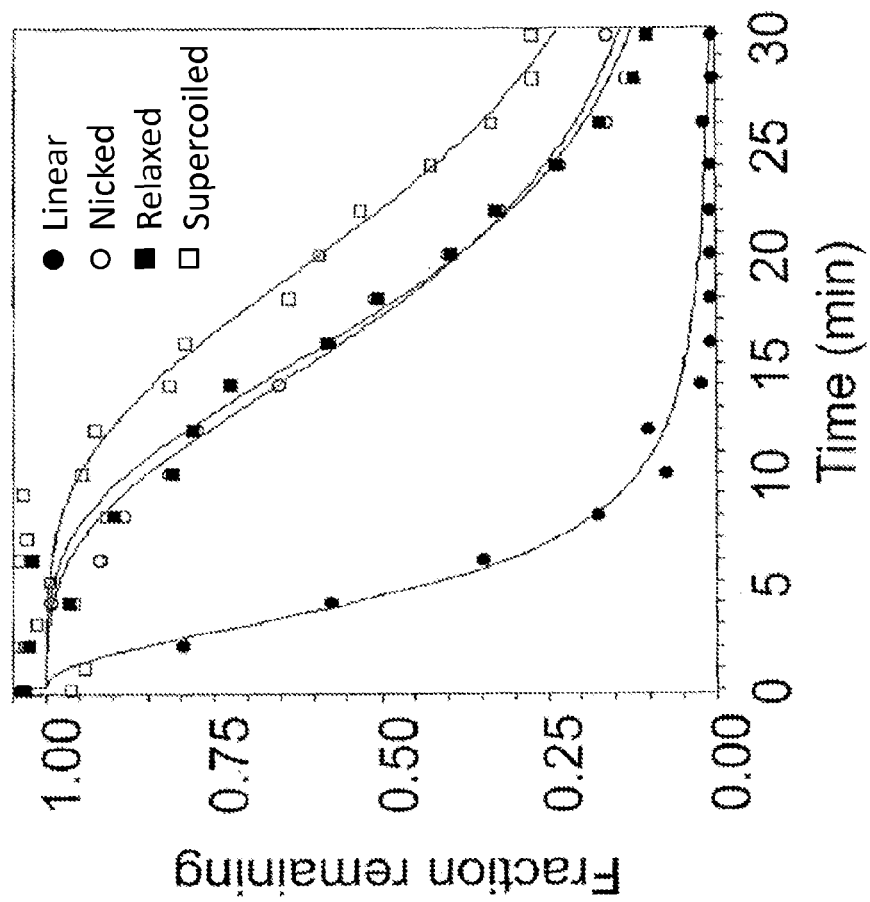
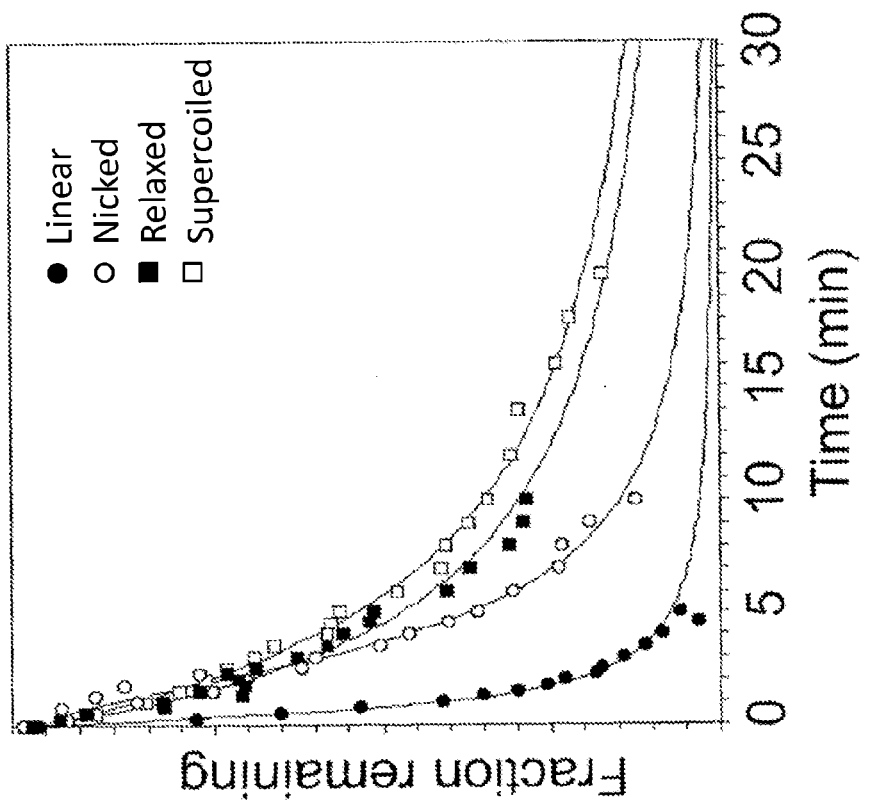

SUPERCOILED MINIVECTORS™ FOR GENE THERAPY APPLICATIONS

RELATED APPLICATION

This application claims the benefit of U.S. Provisional Application No. 61/252,455, filed on Oct. 16, 2009. The entire teachings of the above application are incorporated herein by reference.

GOVERNMENT SUPPORT

The invention was supported, in whole or in part, by grant number R01-AI054830 from the National Institutes of Health. The Government has certain rights in the invention.

BACKGROUND OF THE INVENTION

Gene therapy involves the delivery of DNA or RNA to diseased organ or cells to correct defective genes implicated in disease. This may be achieved through a number of different approaches. If the condition is due to an absent or non-functional gene product, a functional copy of the gene may be delivered to the disease loci. Alternatively, gene expression may be controlled using RNA interference technologies such as small interfering RNA (siRNA), short hairpin RNA (shRNA) and microRNA (miRNA). RNA interference (RNAi), a natural cell process by which specific mRNAs are targeted for degradation by complementary small interfering RNAs (siRNAs), enables the specific silencing of a single gene at the cell level. A variety of biomedical[1] and clinical research[2-4] have showed that RNAi has a great potential as an efficient therapeutic approach. Typically, RNA interference is used to down-regulate expression of a pathogenic gene, however, up-regulation of genes is possible by targeting regulatory regions in gene promoters[15].

Despite the tremendous therapeutic potential of gene therapy and the large number of disorders identified as good candidates, the field has so far been unsuccessful. These failures are largely due to complications associated with gene delivery. Delivery efficiency is high for viral vectors, the most common delivery method; however, these have limited therapeutic potential because of problems observed in clinical trials including toxicity, immune and inflammatory responses, difficulties in targeting and controlling dose. In addition, there is justifiable concern that the vectors will integrate into the genome, with unknown long-term effects, and the possibility that the virus may recover its ability to cause disease.

Much effort has therefore been directed towards non-viral vector systems, such as plasmid DNA. These vectors are attractive because they are simple to produce and store, and can stably persist in cells; however, they contain bacterial DNA sequences that may trigger immunotoxic responses. Some human cells, including dendritic cells and T-cells, cannot be efficiently transfected with current plasmid vectors. Short, linear DNA vectors and small RNAs such as short interfering RNA (siRNA) and micro-RNA (miRNA) are more easily introduced into cells than plasmids. Linear DNA and RNA ends, however, trigger rapid degradation by cells, therefore requiring continuous replenishment. Furthermore, the DNA ends can signal repair and recombination pathways to cause apoptosis. For these reasons, RNAi- and miRNA-based technologies have not yet been highly successful in the clinic. There is clearly a desperate need for a new and efficient way to therapeutically deliver gene therapy vectors to cells.

Plasmid DNA vectors have some utility in basic research because they are straightforward to generate and isolate. They are propagated in bacterial strains and recovered from the bacterial cells. As mentioned above, however, this requires them to contain bacterial DNA sequences, notably a prokaryotic origin of replication and an antibiotic resistance marker for maintenance of the plasmid. The presence of these bacterial sequences has a number of very serious and deleterious consequences. Most notably, it limits how small the plasmids can be made. Large plasmids, of several kbp, are transfected at very low efficiency. Their large size also makes them to susceptible to hydrodynamic shearing forces associated with delivery (e.g., through aerosolisation) or in the bloodstream. Shear-induced degradation leads to a loss of biological activity that is at least partially responsible for the current lack of success in using non-viral vectors for gene therapy. Various cationic and liposomal transfection reagents have been designed to try and alleviate these problems with transfection, but these suffer from problems with cytotoxicity. In addition, the bacterial sequences on plasmids can induce silencing of the gene carried on the plasmid[14] leading to loss of efficacy even if the plasmid is successfully transfected. The CpG motifs that are more common in bacterial than eukaryotic DNA sequences also elicit immune responses in mammalian cells. Reducing the size of DNA vectors appears to be a reasonable approach to increase cell transfection efficiency. One may envision that the bacterial sequences on the plasmid could be physically removed and resultant short linear DNA fragments that contain only the therapeutic sequences more easily introduced into cells than conventional plasmid vectors. Unfortunately, the ends of linear DNA are highly bioreactive in vivo, triggering cellular DNA repair and recombination processes as well as apoptosis. Thus, there is a need for gene targeting therapies that are stable in biological environments and that allow for greater cell transfection and transgene expression.

SUMMARY OF THE INVENTION

The invention provides a nucleic acid molecule composition comprising a MiniVector, wherein said MiniVector encodes a nucleic acid sequence. In one embodiment, the nucleic acid sequence encoded by the MiniVector comprises short hairpin RNA (shRNA). In a further embodiment, the nucleic acid sequence encoded by the MiniVector comprises micro RNA (miRNA). In yet another embodiment, the nucleic acid sequence encoded by the MiniVector comprises a gene. In an additional embodiment, the nucleic acid sequence encoded by the MiniVector comprises DNA that can be bound by another cellular component, such as by protein, a different DNA sequence, an RNA sequence, or a cell membrane.

In any embodiment, the MiniVectors can be labeled if desired with a chemical moiety (e.g., cholesterol, fluorescein, biotin, a dye, or other moiety); alternatively or in addition, additional modifications such as modified bases or modified backbones can also be included.

In another embodiment, the invention provides a method of silencing expression of a gene in a cell comprising contacting said cell with a MiniVector, wherein said MiniVector encodes a nucleic acid sequence, wherein the nucleic acid sequence silences the expression of the gene. In one embodiment, embodiment, the nucleic acid sequence encoded by the Mini-Vector comprises short hairpin RNA (shRNA). In a further embodiment, the nucleic acid sequence encoded by the Mini-Vector comprises micro RNA (miRNA). In yet another embodiment, the nucleic acid sequence encoded by the Mini- Vector comprises a gene. In an additional embodiment, the nucleic acid sequence encoded by the MiniVector comprises DNA that can be bound by another cellular component, such as by protein, a different DNA sequence, an RNA sequence, or a cell membrane. In any embodiment, the MiniVectors can be labeled if desired as described above (e.g., with a chemical moiety, and alternatively or in addition, with a modified base and/or modified backbone.) In a further embodiment, the cell is a mammalian (e.g., a human) cell.

In one embodiment, the invention relates to a method of gene therapy, comprising administering a therapeutically effective amount of a MiniVector to a mammal in need thereof, wherein the MiniVector encodes a nucleic acid sequence. In one embodiment, embodiment, the nucleic acid sequence encoded by the MiniVector comprises short hairpin RNA (shRNA). In a further embodiment, the nucleic acid sequence encoded by the MiniVector comprises micro RNA (miRNA). In yet another embodiment, the nucleic acid sequence encoded by the MiniVector comprises a gene. In an additional embodiment, the nucleic acid sequence encoded by the MiniVector comprises DNA that can be bound by another cellular component, such as by protein, a different DNA sequence, an RNA sequence, or a cell membrane. In any embodiment, the MiniVectors can be labeled if desired as described above (e.g., with a chemical moiety, and alternatively or in addition, with a modified base and/or modified backbone). In a further embodiment, the mammal is a human.

In another embodiment, the invention relates to a method of gene therapy, comprising administering to a cell a therapeutically effective amount of a MiniVector, wherein the MiniVector encodes a nucleic acid sequence. In one embodiment, the nucleic acid sequence encoded by the MiniVector comprises short hairpin RNA (shRNA). In a further embodiment, the nucleic acid sequence encoded by the MiniVector comprises micro RNA (miRNA). In yet another embodiment, the nucleic acid sequence encoded by the MiniVector comprises a gene. In an additional embodiment, the nucleic acid sequence encoded by the MiniVector comprises DNA that can be bound by another cellular component, such as by protein, a different DNA sequence, an RNA sequence, or a cell membrane. In any embodiment, the MiniVectors can be labeled if desired as described above (e.g., with a chemical moiety, and alternatively or in addition, with a modified base and/or modified backbone). In yet another embodiment, the cell is a mammalian (e.g., a human) cell.

In another embodiment, the invention relates to a method of gene therapy, comprising delivery to cells in the respiratory tract of a mammal, a therapeutically effective amount of a MiniVector, wherein the MiniVector encodes a nucleic acid sequence. The MiniVector can be administered to the respiratory tract by the use of a nebulization device, and can be administered in the absence of a carrier molecule. In one embodiment, the MiniVector can be administered to the nasal mucosa of the respiratory tract of the mammal. In these embodiments, the nucleic acid sequence encoded by the MiniVector can comprise short hairpin RNA (shRNA) or micro RNA (miRNA). In other embodiments, the nucleic acid sequence encoded by the MiniVector comprises a gene. In an additional embodiment, the nucleic acid sequence encoded by the MiniVector comprises DNA that can be bound by another cellular component, such as by protein, a different DNA sequence, an RNA sequence, or a cell membrane. In any embodiment, the MiniVectors can be labeled if desired as described above (e.g., with a chemical moiety, and alternatively or in addition, with a modified base and/or modified backbone.)

In a further embodiment, the invention relates to a method of silencing anaplastic lymphoma kinase gene expression in a mammalian cell, comprising administering to the mammalian cell an effective amount of MiniVector, wherein the MiniVector encodes a nucleic acid sequence, and wherein the MiniVector silences anaplastic lymphoma kinase gene expression. In one embodiment, the nucleic acid sequence encoded by the minivector comprises short hairpin RNA (shRNA). In a further embodiment, the nucleic acid sequence encoded by the minivector comprises micro RNA (miRNA). In yet another embodiment, the nucleic acid sequence encoded by the MiniVector comprises a gene. In an additional embodiment, the nucleic acid sequence encoded by the MiniVector comprises DNA that can be bound by another cellular component, such as by protein, a different DNA sequence, an RNA sequence, or a cell membrane. In any embodiment, the minivectors can be labeled if desired as described above (e.g., with a chemical moiety, and alternatively or in addition, with a modified base and/or modified backbone). In yet another embodiment, the mammalian cell is a human cell.

In one embodiment, the invention relates to a method of treating cancer in a mammal in need thereof, comprising administering to the mammal a therapeutically effective amount of a MiniVector, or a mammalian cell comprising a MiniVector, wherein the MiniVector encodes a nucleic acid sequence. In one embodiment, embodiment, the nucleic acid sequence encoded by the MiniVector comprises short hairpin RNA (shRNA). In a further embodiment, the nucleic acid sequence encoded by the MiniVector comprises micro RNA (miRNA). In yet another embodiment, the nucleic acid sequence encoded by the MiniVector comprises a gene. In an additional embodiment, the nucleic acid sequence encoded by the MiniVector comprises DNA that can be bound by another cellular component, such as by protein, a different DNA sequence, an RNA sequence, or a cell membrane. In any embodiment, the minivectors can be labeled if desired as described above (e.g., with a chemical moiety, and alternatively or in addition, with a modified base and/or modified backbone.) In a further embodiment, the mammal is a human. In one embodiment, the cancer is non-Hodgkin's lymphoma. In yet another embodiment, the non-Hodgkin's lymphoma is anaplastic large cell lymphoma.

In another embodiment, the invention relates to a method of gene expression in a cell comprising contacting said cell with a MiniVector, wherein said MiniVector encodes a nucleic acid sequence, wherein the nucleic acid sequence expresses the gene. In one embodiment, the nucleic acid sequence comprises a gene. In another embodiment, the cell is a mammalian (e.g., a human) cell.

BRIEF DESCRIPTION OF THE DRAWINGS

The foregoing will be apparent from the following more particular description of example embodiments of the invention as illustrated in the accompanying drawings in which like reference characters refer to the same parts throughout the different views. The drawings are not necessarily to scale, emphasis instead being placed upon illustrating embodiments of the present invention.

FIG. 3A shows silencing of the cellular ALK gene. To validate potential therapeutic value for the hard-to-transfect Karpas 299 cells were transfected with pMC vector control, a non-relevant control siRNA, conventional pMC-H1-ALK/shRNA plasmid vector, the ALK MiniVector, and synthesized siRNA specific for ALK. Four days after transfection, cellular ALK fusion protein expression was examined by flow cytometry with FITC-conjugated anti-ALK antibody and calculated by mean fluorescence intensity of antibody that bond to cellular ALK proteins. FIG. 3B shows inhibition of lymphoma cell growth. Meanwhile, resultant change in cell growth was also simultaneously studied by MTT cell proliferation assay at day 4 after cell transfection. Relative growth in cells with each treatment was shown in the graph. ** $P<0.01$.

(FIG. 8A) The curves represent the fit to a sigmoidal function. Nebulization survival times were determined for each DNA vector. The time at which 50% of the vector survived ($Survival_{50}(Neb)$) was plotted (FIG. 8B). Each $Survival_{50}(Neb)$ value is the mean from at least three separate experiments. Error bars represent the standard deviation. FIGS. 9A-B depicts the influence of DNA topology on DNA survival. FIG. 9A shows how topology of plasmid DNA (1,873 bp) influences its survival during nebulization. The fraction of DNA vector of each topology at each timepoint is shown. The curves are shown fitted to a sigmoidal function. Circular plasmids lasted much longer than linear DNA. Supercoiling provided additional resistance to shear forces. FIG. 9B shows how topology of Minivector (999 bp) influences its survival during sonication. The fraction of DNA was quantified the same as in FIG. 9A. Supercoiled Minivector survived significantly longer than nicked or linear DNA.

DETAILED DESCRIPTION OF THE INVENTION

Figure 1:
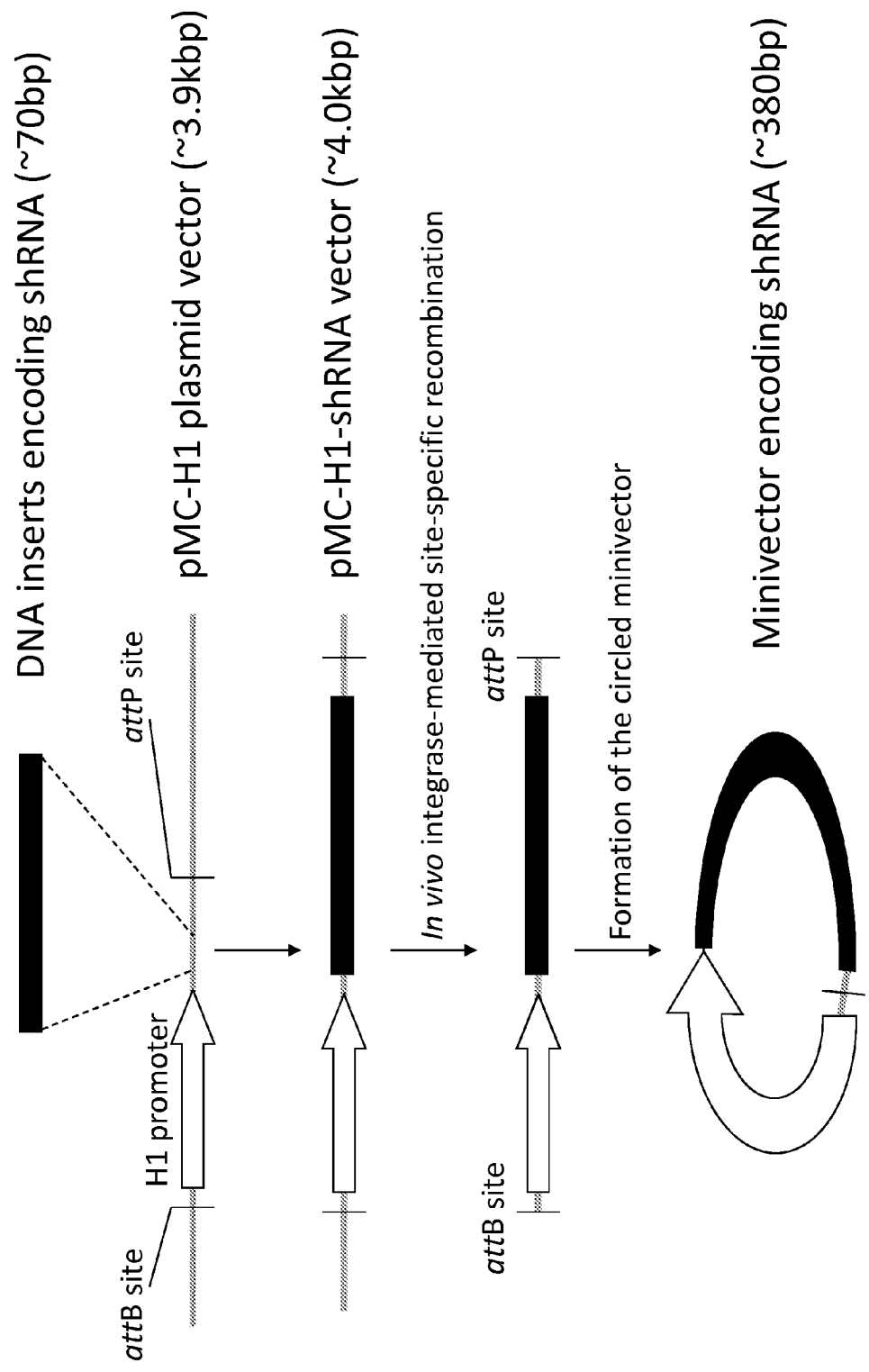
FIG. 1 shows the preparation of MiniVector encoding shRNA for gene silencing. The synthesized oligo DNA encoding shRNA was subcloned into the modified pMC-H1 vector under control of H1 promoter. By undergoing integrase-mediated recombination, the circular minivectors composed of only H1 promoter and sequences for shRNA with a size of about 385 bp were generated.

The invention described herein, MiniVector for use in alteration of gene expression (including silencing expression of a gene or causing expression of a gene), such as for gene therapy, holds exciting promise. Because the circular DNA persists in cells, continuous, renewable shRNA or miRNA or transgene expression is possible. The invention described herein relates to a novel, non-viral gene-therapy vector, MiniVector, small, supercoiled DNA vectors which are almost completely devoid of bacterial sequences. Because of their small size, these MiniVectors are transfected with high efficiency. The lack of bacterial sequence allows for persistent transgene expression with reduced silencing and immune responses associated with plasmid DNA vectors.

In the first instance, the MiniVectors were tested for their ability to deliver a minimal construct comprising a promoter and sequences encoding for shRNA to mediate gene silencing. RNA interference mediated gene silencing may alternatively be induced by delivering synthesized small interfering RNAs. These RNAs are highly susceptible to environmental nucleases, however, and only produce a very transient response therefore reducing their therapeutic value. In contrast, DNA vectors are relatively stable in biological environments. Therefore, as alternatives DNA vector systems that can express shRNA have been developed for gene-targeting therapy.[5] DNA vectors encoding for shRNA have cellular effects significantly longer than that achieved by synthesized siRNA and the targeted gene can be down-regulated for several months.[6] Moreover, the inducible shRNA expression system makes DNA vectors more tractable.[7]

The MiniVectors are, however, not limited to being a vehicle for shRNA (or miRNA). Because of the versatility that arises from not requiring a large antibiotic resistance gene and origin of replication the MiniVectors can be engineered to contain a small gene (in this case Gaussia Luciferase) and promoter yet still maintain a small size (less than, for example, about 2000 bp, much smaller than any plasmid bearing a functional gene for gene therapy). Transfection of Gaussia Luciferase encoding MiniVectors into human dendritic cells and T-cells resulted in much higher gene expression in comparison to the regular plasmid containing the same gene and promoter. These results show two significant things. First, MiniVectors can be used to deliver small genes that can be transcribed and translated into functional proteins. Second, and demonstrating the great promise of these vectors, the MiniVector can transfect dendritic cells and T-cell lines in which non-viral transfection has had little to no success previously.

In addition, the MiniVectors overcome a key challenge of gene therapy: targeting the vector to the diseased organ. For example, while lungs are amenable to gene therapy because they are readily accessible, nebulization to create an aerosol for drug delivery causes extensive shearing, rendering vectors such as plasmid DNA ineffective. However, the MiniVectors survived shearing forces upon nebulization, even in the absence of condensing agents, indicating their efficacy for targeted delivery to lung tissue.

Supercoiled DNA minicircles and methods for producing minicircles have been described in U.S. application Ser. No. 11/448,590 (US Publication No.: US 20070020659 A1); Title: "Generation of Minicircle DNA With Physiological Supercoiling", by Zechiedrich et al., which is incorporated herein by reference in its entirety. For gene therapy applications, supercoiled minicircles are referred to herein as "Mini-Vectors." As described herein, MiniVectors were tested and found to have biostability, a high cell transfection rate, high gene silencing capacity and were found to have therapeutic potential in gene therapy. The findings described herein demonstrate that the MiniVectors possess advantages for gene therapy.

As used herein "MiniVector" refers to a mini-sized and circular DNA vector system (minicircle) and has been previously described in U.S. application Ser. No. 11/448,590 (US Publication No.: US 20070020659 A1); Title: "Generation of Minicircle DNA With Physiological Supercoiling", by Zechiedrich et al., which is incorporated herein by reference in its entirety. MiniVector are supercoiled, circular DNA molecules which are obtained in *E. coli* by in vivo integrase-mediated site-specific recombination. They comprise, for example, a nucleic acid molecule with merely the transgene expression cassette (including promoter and a nucleic acid sequence, wherein the nucleic acid sequence can be, for example, a sequence encoding for shRNA targeted to a specific mRNA transcript, or the nucleic acid sequence can be a gene encoding for expression of a specific protein) and, importantly, minimal bacterial-originated sequences.[8,9,10]

MiniVectors for use in gene therapy are double-stranded, circular DNA molecules of the size of from about 100 base pairs (bp) to about 2.5 kilo base (kb), such as from about 200 bp to about 2.2 kb, for example from about 300 bp to about 2.0 kb, for example from about 400 bp to about 1.9 kb, for example from about 500 bp to about 1.8 kb, for example from about 600 bp to about 1.7 kb, for example from about 700 bp to about 1.6 kb, for example from about 800 bp to about 1.5 kb, for example from about 900 bp to about 1.4 kb, for example from about 1 kb to about 1.3 kb, for example from about 1.1 kb to about 1.2 kb. MiniVectors can be made in size increments of about 100 bp or fewer.

The MiniVectors can be labeled, e.g., using a chemical moiety, as desired. Representative labels include fluorescein, biotin, cholesterol, dyes, modified bases and modified backbones. Representative dyes include: 6-carboxyfluorescein, 5-/6-carboxyrhodamine, 5-/6-Carboxytetramethylrhodamine, 6-Carboxy-2'-,4-,4'-,5'-,7-,7'-hexachlorofluorescein), 6-Carboxy-2'-,4-,7-,7'-tetrachlorofluorescein), 6-Carboxy-4'-,5'-dichloro-2'-,7'-dimethoxyfluorescein, 7-amino-4-methylcoumarin-3-acetic acid), Cascade Blue, Marina Blue, Pacific Blue, Cy3, Cy5, Cy3.5, Cy5.5, IRDye700, IRDye800, BODIPY dye, Texas Red, Oregon Green, Rhodamine Red, Rhodamine Green. Additional modifications can also include modified bases (e.g. 2-aminopurine, methylated bases), or modified backbones (e.g., phosphorothioates, where one of the non-bridging oxygens is substituted by a sulfur; 2'-O-methyl-RNA-oligonucleotides; methyl-phosphate oligonucleotides). Multiple labels, including chemical moieties and/or modified bases and/or modified backbones, can be used simultaneously, if desired. Methods of labeling nucleotides are described, for example, in "Nucleic Acid Probe Technology" by Robert E. Farrell; RNA Methodologies (Third Edition), 2005, pp. 285-316; and "Enzymatic Labeling of Nucleic Acids" by Stanley Tabor and Ann Boyle, in Current Protocols in Immunology 2001 May; Chapter 10:Unit 10.10. The teachings of these references are incorporated herein by reference in their entirety.

As used herein, the term "RNA interference," or "RNAi," refers to the process whereby sequence-specific, post-transcriptional gene silencing is initiated by an RNA that is homologous in sequence to the silenced gene. RNAi, which occurs in a wide variety of living organism and their cells, from plants to humans, has also been referred to as post-transcriptional gene silencing (PTGS) and co-suppression in different biological systems. The sequence-specific degradation of mRNA observed in RNAi, is mediated by small (or short) interfering RNAs (siRNAs).

As used herein, the term "interfering RNA" means an RNA molecule capable of directing the degradation of an RNA transcript having a nucleotide sequence at least a portion of which is substantially the same as that of the interfering RNA, through the mechanism of RNA interference (RNAi). As known in the art, interfering RNAs can be "small interfering RNAs," or siRNAs, composed of two complementary single-stranded RNAs that form an intermolecular duplex. Interfering RNAs can also be "short hairpin RNAs," or shRNAs, composed of a single-stranded RNA with two self-complementary regions that allow the RNA to fold back upon itself and form a stem-loop structure with an intramolecular duplex region and an unpaired loop region.

As used herein, the term "gene silencing" refers to a reduction in the expression product of a target gene. Silencing may be complete, in that no final gene product is produced, or partial, in that a substantial reduction in the amount of gene product occurs.

Mammal, as used herein, refers to animals, including, but not limited to, primates (e.g., humans), cows, sheep, goats, horses, pigs, dogs, cats, rabbits, guinea pigs, rats, mice or other bovine, ovine, equine, canine, feline, rodent or murine species. In one embodiment, the mammal is a human.

Mammalian cell, as used herein, refers to cells from animals, including, but not limited to, primates (e.g., humans), cows, sheep, goats, horses, pigs, dogs, cats, rabbits, guinea pigs, rats, mice or other bovine, ovine, equine, canine, feline, rodent or murine species. In one embodiment, the mammalian cell is a human cell.

The term "treating" includes both therapeutic treatment and prophylactic treatment (reducing the likelihood of development). The term means decrease, suppress, attenuate, diminish, arrest, or stabilize the development or progression of a disease (e.g., a disease or disorder delineated herein), lessen the severity of the disease or improve the symptoms associated with the disease.

As described herein, the MiniVector for use in gene therapy is present in an effective amount. As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

As described herein, the circular DNA MiniVector system, composed of an H1 promoter and the sequences encoding shRNA for gene therapy was tested. The biostability, cell transfection rate, and gene silencing capacity of the MiniVector systems was compared to the conventional DNA plasmid vectors and the synthesized siRNA. In addition, therapeutic potential of the MiniVector was tested in the hard-to-transfect suspension Jurkat (lymphoma/leukemia) cells and Karpas 299 (human anaplastic large cell lymphoma (ALCL)) cells. ALCL cells carry an abnormal chromosomal translocation involving the anaplastic lymphoma kinase (ALK) gene (1-3). The resultant abnormal expression of a chimeric ALK fusion protein (4-6) has been demonstrated to be a key pathogenesis factor for ALCL development (7-9). In this study, effects of the MiniVectors on cellular ALK gene expression and lymphoma cell growth were simultaneously examined.

The biostability assays showed that the MiniVector was stable in human serum for over 24 hours and, in contrast, the synthesized siRNA was completely digested after 4 30 min incubation. For cell transfection studies, the MiniVector encoding GFP shRNA was introduced into stable GFP-expressing cells with Lipofectamine® methodology. Flow cytometry analysis revealed that transfection of the MiniVector could induce significant GFP gene silencing in both 293FT cells (52% reduction) and the hard-to-transfect Jurkat suspension lymphoma cells (46% reduction). To test potential therapeutic value, a MiniVector was generated for silencing of the anaplastic lymphoma kinase (ALK) gene, which is a key pathogenic factor of human anaplastic large cell lymphoma (ALCL). Cultured Karpas 299 ALCL cells were transfected with the MiniVector, conventional plasmid vector, and synthesized siRNA and resultant gene silencing was monitored by flow cytometry with FITC-conjugated anti-ALK antibodies. A significant decrease of ALK protein expression was detected in the cells transfected with the MiniVector (25% reduction) as well as the synthetic siRNA (26% reduction), 30-fold higher than that induced by the conventional plasmid (0.8% reduction). Furthermore, simultaneous MTT assays demonstrated a significant growth arrest of ALCL cells (P<0.01) induced by the MiniVector or synthesized siRNA, but not conventional plasmid. Findings indicate that the Mini-Vector system is stable in serum and has a high cell transfection capacity, suggesting potential value for in vivo gene therapy particularly in the hard-to-transfect cells.

As also described herein, MiniVectors and plasmids varying from under 300 to over 5,000 base pairs were subjected to shear forces generated by aerosolization through a nebulizer or sonication. Both supercoiling and length dramatically impacted shear force survival. DNA supercoiling protected DNA from shearing. Interestingly, a nicked molecule was sheared equivalently to a relaxed, intact DNA. DNA shearing was inversely correlated with DNA length; the shorter the DNA, the more resistant the DNA was to shearing. Even in the absence of condensing agents, supercoiled DNA less than 1,200 base pairs survived for a time equal to the typical treatment regimen time for some therapies. These results provide an indication of the potential value of MiniVectors for targeted delivery for gene therapy.

In addition to gene therapy applications, MiniVectors can also be used to study DNA supercoiling, DNA supercoiling-dependent alternative structures, or DNA supercoiling-dependent protein mechanisms. For example, an insert containing sequence from the disease locus, spinocerebellar ataxia type 1, including a 59 CAG repeat tract, was cloned into a 582 bp MiniVector. A limited but significant amount of cleavage by T7 endonuclease I was detected at higher supercoiling levels, suggesting the presence of supercoil-stabilized alternative structures.

MiniVectors can also be used as assays to evaluate the mechanisms of antibiotics and anticancer drugs that target DNA topoisomerases. Further, MiniVectors can be used to regulate genes implicated in disease and in the genetic modification of human dendritic cells and human T-cells.

In all of the embodiments described herein, a wide variety of cell types or organisms can be used. For example, mammals, as described above can be used. Alternatively, other types of cells/organisms can be used, including bacteria, Archaea, and eukaryotes (e.g., plants).

In all of the embodiments described herein, it is also possible to use multiple types of minivectors in a single system, as well as minivectors with multiple targets. For example, two (or more) separate minivectors can be designed, in which each individual MiniVector encodes a different nucleic acid sequence that comprises a portion or a domain of a single protein, such that when the individual minivectors are expressed in a single cell, the portions or domains come together to form a single active protein. In addition, polymer forms of minivectors can also be formed during in vivo recombination. Moreover, it is possible to insert sequences encoding multiple therapeutic shRNAs and produce a MiniVector with simultaneous multi-gene targeting potential in the transfected cells, resulting in a highly sensitive and specific gene therapy.

A description of embodiments of the invention follows.

EXAMPLES

Example 1

Cell Transfection and Gene Silencing

Materials and Methods
Oligonucleotide Synthesis and MiniVector Preparation

For GFP silencing the synthetic siRNAs were purchased with paired control siRNA (catalog #AM4626 from Ambion, Foster city, CA). The siRNA for the ALK gene was synthesized according to the reported sequences[11] with sense: (SEQ ID NO: 1) 5'-CACUUAGUAGUGUACCGCCtt-3' and (SEQ ID NO: 2) antisense: 5'-GGCGGUACACUACUAAGUGtt-3' by Ambion. The parent plasmid used to generate the shRNA expressing minivector was generated as follows. KasI and HindIII restriction sites were engineered into pMC339-BbvCI (Fogg et al. 2006). A H1 promoter was subcloned into the pMC vector by inserting the KasI/HindIII fragment containing H1 promoter and shRNA expressing sequence from pSUPER-CCR5shRNA-3 (refs) between the KasI and HindIII sites. A BglII site was subsequently engineered in front of the shRNA expression sequence to generate pMV-CCR5shRNA3-BglII. This allows the shRNA expression sequences to be readily exchanged by inserting between the BglII and HindIII sites (FIG. 1). The DNA inserts encoding GFP shRNA with sense sequence of 5'-GATCCCCG-CAAGCTGACCCTGAAGTTCTTCAA-GAGAGAACTTCAGGGTCAG CTTGCTTTTTA [12] and ALK shRNA with sense sequence of 5'-GATCCCCGAGT-TGGTCATTGCGAGGATGCCATTTCAA-GAGAATGGTATCCTC GTAATGACCAGCTCTTTTTA (Ito M, Zhao N, Zeng Z, Chang C C, Zu Y. Cancer Gene Ther 2010; 17: 633-644.) were each synthesized as two oligonucleotides, annealed to form suplexes and subcloned into the modified pMV vector under H1 promoter control between BglII and BamHI sites (FIG. 1). The resulting plasmids were named pMV-H1-GFPshRNA and pMV-H1-ALKshRNA. MiniVector parent plasmids were transformed into E. coli strain LZ54 (Zechiedrich et al. (1997), Genes Dev. 11, 2580-2592), and large scale λ-integrase (Int) mediated recombination was performed as described previously[13] with the following minor modification. Pure, supercoiled, monomeric, MiniVector was isolated by multiple rounds of gel Sephacryl S-500 filtration (GE Healthcare Life Sciences, Piscataway, N.J.). Only the supercoiled, monomeric form of MiniVector was used for the gene silencing study. Along the convention of "p" in front of plasmid names, we designate MiniVector with "mv" and the parent plasmids used to generate MiniVectors are designated "pMV".

Biostability Assays

The generated MiniVector encoding GFP shRNA (1 µg) as well as equimass amounts of parental plasmid pMV-H1-GFPshRNA and synthetic GFP siRNA were incubated at 37° C. in 100 µl of 100% human serum (Atlanta Biological Inc. Lawrenceville Ga.). At various time points, residual DNA vectors or siRNA products were extracted with phenol:chloroform:isoamyl alcohol (25:24:1), extracted with chloroform, and precipitated in 95% ethanol. The residual RNA and DNA products were then examined on 10% polyacrylamide and 1.5% agarose gels, respectively, followed by ethidium bromide staining. The bands of DNA or siRNA products were quantified using TotalLab software (FotoDyne Inc., Hartland, Wis.), and plotted using Kaleidagraph (Synergy Software, Reading, Pa.).

Cell Transfection and Gene Silencing

As a reporter system for GFP gene silencing, the stable GFP-expressing cells were established, derived from adhesion 293FT cells (a transformed human embryonic kidney cell line, Invitrogen) and the hard-to-transfect Jurkat cells (a human leukemia/lymphoma cell line). The GFP-expressing cells were transfected with MiniVectors, plasmids, or siRNAs using Lipofectamine® methodology following the manufacturer's instructions (Invitrogen, Carlsbad, Calif.). Resultant silencing of cellular GFP expression was quantified by flow cytometry at day 3 and data was analyzed with FlowJo software (BD Biosciences, San Jose, Calif.). Changes in mean fluorescence intensity of cellular GFP were calculated by using the untreated cells as control (%).

In addition, cultured Karpas 299 cells (a human ALCL cell line) were transfected with the synthetic ALK siRNA and control siRNA, pMV-H1 vector, pMV-H1-ALKshRNA, or ALK MiniVector (mv-H1-ALKshRNA) as described above. Cells were collected at day 3, fixed, and permeabilized using a cell preparation kit from BD Biosciences according to the manufacturer's instructions. Cellular ALK fusion proteins were stained by FITC-conjugated anti-ALK antibody (1:20 dilution, BD Biosciences) and quantified by flow cytometry.

MTT Cell Proliferation Assay

Cellular ALK gene silencing and changes in cell growth/proliferation were simultaneously examined. Aliquots of the transfected Karpas 299 cells (100 W/sample) were transferred to a 96-well plate, mixed with 10 µl of assay buffer of the MTT assay kit from Chemicon International (Temecula, CA), incubated at 37° C. for 4 hours, and then lysed per manufacturer's instructions. MTT cell proliferation assay was analyzed using a BioRad microplate reader by the detected absorbance at $OD_{540}$ in each specimen. Relative cell growth (%) was calculated by using untreated cells as a background control. All experiments were performed at least three times, and the results were presented with mean±standard deviation.

Results

The MiniVectors, were Stable in Human Serum

To generate minivectors the synthetic oligo DNAs encoding shRNA specific for the GFP gene or the ALK gene were subcloned into the modified pMV-H1 parent plasmid (FIG. 1)[13]. By undergoing in vivo integrase-mediated recombination, circular minivectors, ~385 bp, that contain barely H1 promoter, sequences for shRNA, and are almost completely devoid of bacterial sequence, were obtained. For the gene silencing study, the monomeric and supercoiled form of the MiniVectors was fractioned and purified.

For the biostability study, the purified GFP MiniVectors were incubated in 100% human serum at 37° C. for 3 days. In control groups, parental pMV-GFPshRNA vector and synthetic GFP siRNA were tested in the same condition. At various time points, residual DNA vectors and synthetic siRNA were extracted and analyzed by electrophoresis. The MiniVectors were stable in human serum for at least 48 hours whereas the parental plasmid DNA of vector was more than 50% degraded after ~4 hours. In contrast, the synthetic siRNA was digested in less than 30 minutes.

Figure 2:
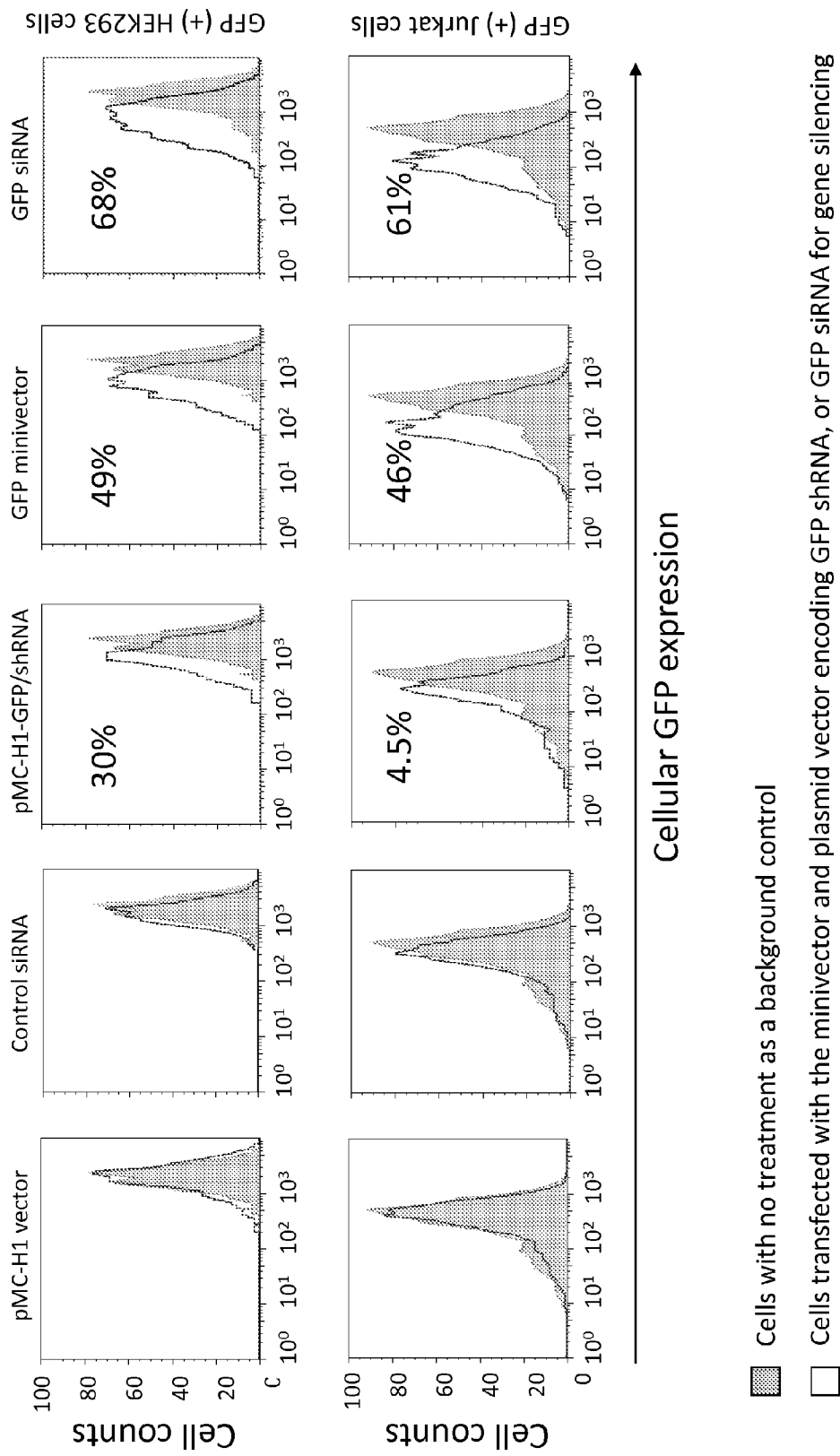
FIG. 2 shows the high cell transfection/gene silencing capacity of the minivectors in the hard-to-transfect lymphoma cells. Upper row, the stable GFP-expressing adhesion 293FT cells were transfected with the MiniVector, synthetic siRNAs, or DNA plasmid vectors by Lipofectamine method for gene silencing. After being incubated for 3 days, flow cytometry was performed and the change in mean fluorescence intensity of cellular GFP expression was compared to that of the untreated cells (100%). Lower row, the same set of treatments was also carried out in the hard-to-transfect Jurkat cells (a human T-lymphoma/leukemia cell line from ATCC, Manassas, Va., USA) and resultant change in cellular GFP expression was calculated.

High Gene Silencing Efficiency of the Minivector in the Hard-to-Transfect Lymphoma Cells To evaluate cell transfection potential for gene silencing, two types of stably GFP-expressing cells derived from adhesion 293FT cells (a transformed human kidney fibroblast cell line) and from suspension Karpas 299 cells (a human ALCL cell line) were used. The GFP-expressing cells were transfected with the GFP shRNA MiniVector by using Lipofectamine® methodology and resultant changes in cellular GFP expression were quantified by flow cytometry 3 days after transfection as described in 'Materials and Methods'. In the adhesion 293FT cells, transfection of the MiniVector induced significant GFP gene silencing (49%), which was comparable to that induced by pMV-H1-GFPshRNA plasmid vector (30%) and the synthetic GFP siRNA (68%) (Upper row of FIG. 2). Interestingly, in the hard-to-transfect Jurkat cells, transfection of MiniVector resulted in a significant silencing of the GFP gene (a 46% reduction of cellular eGFP expression), which was 10-fold higher than that induced by pMV-H1-GFPshRNA plasmid vector (4.5%) and only slightly lower than that by the synthetic GFP siRNA (61%) (Lower row of FIG. 2).

Figure 3:
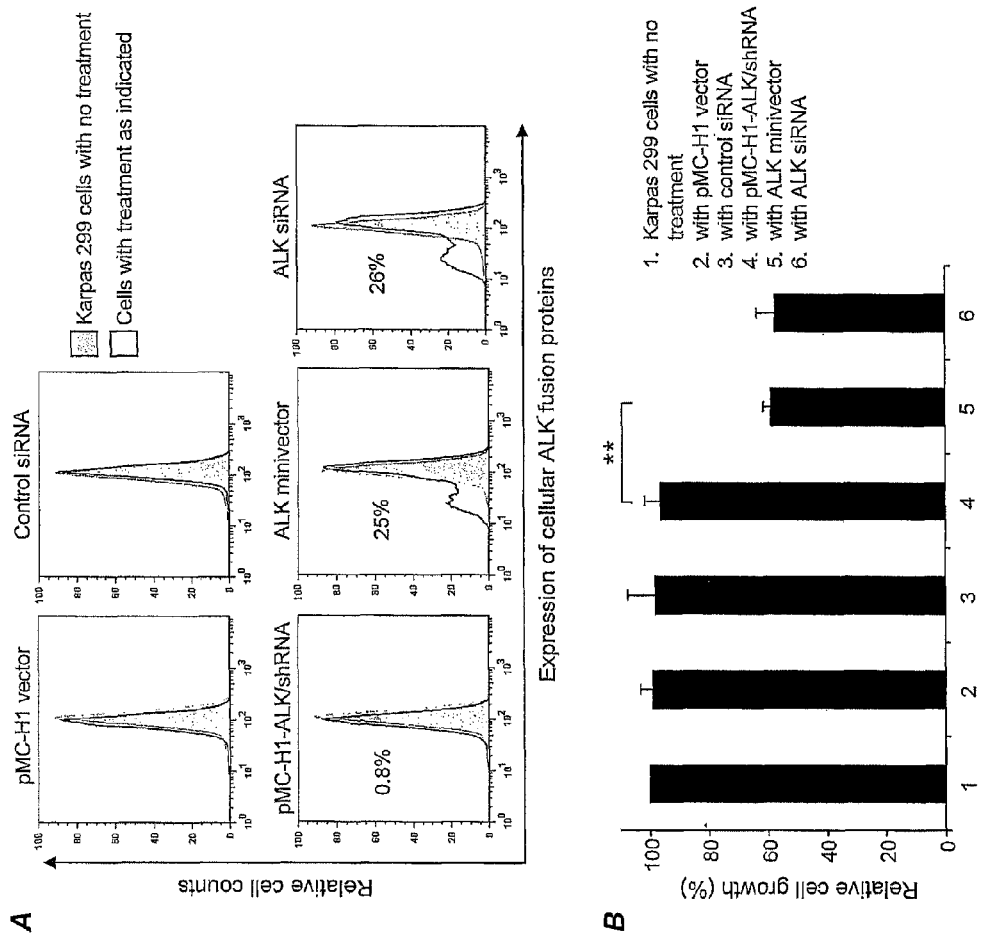
FIGS. 3A-B show the MiniVector-induced ALK gene silencing and growth arrest of Karpas 299 cells ((a human ALCL cell line from the German resource center for biological material (DSMZ).

Silencing the ALK Gene by the Minivector Induced Growth Arrest of Karpas 299 Lymphoma Cells It has been demonstrated that abnormal expression of ALK fusion protein is a key pathogenic factor for development of the ALK-positive ALCL, and siRNA-induced ALK gene silencing resulted in growth inhibition of ALCL cells. To validate a potential therapeutic role for ALCL, the MiniVector encoding ALK shRNA was transfected into the hard-to-transfect Karpas 299 lymphoma cells. Three days after cell transfection, resultant ALK gene silencing was evaluated by quantifying cellular ALK fusion protein expression with flow cytometry using a FITC-conjugated anti-ALK antibody as described above. Transfection of MiniVector resulted in significant silencing of the ALK gene in cultured Karpas 299 cells with a 25% reduction of expression of cellular ALK fusion proteins, which was as efficient as that induced by transfection of the synthetic ALK siRNA (26%) (FIG. 3A). In contrast, conventional plasmid vector of pMV-H1-ALKshRNA had little gene silencing effect in the hard-to-transfect Karpas 299 lymphoma cells, led to a negligible decreased expression (0.8%) of cellular ALK fusion protein. Findings indicated that the MiniVector was 30-fold more efficient than a conventional plasmid vector to induce ALK gene silencing in the hard-to-transfect Karpas 299 lymphoma cells.

In addition, to confirm cellular effect resulting from the induced ALK gene silencing, corresponding cell growth was simultaneously examined for each treatment after 3 days. Relative cell growth (%) was detected by MTT cell proliferation assays as described under 'Materials and Methods'. Transfection of Karpas 299 lymphoma cells with MiniVector encoding ALK/shRNA as well as the synthetic ALK siRNA resulted in a significant inhibition of cell growth (near 40% decrease and P<0.01). In contrast, plasmid vector of pMC-H1-ALK/shRNA had no detected effect on cell growth in comparing to control cells that were transfected with vehicle alone, pMC-H1, or control siRNA (FIG. 3B). Taken together, these findings demonstrate that the MiniVector is a powerful tool for cellular gene silencing, particularly in hard-to-transfect cells.

In this study, the biostability and potential use of MiniVector for gene targeting therapy was validated in the hard-to-transfect lymphoma cells. The findings demonstrate that the minivectors possess advantages over both synthetic siRNAs and conventional plasmid DNA vector: high cell transfection/gene silencing rate (relative to conventional plasmid vector) and high biostability in human serum. In addition, using the MiniVector system also eliminates potential cytotoxicity from backbone bacterial sequences of conventional plasmid vectors. The results suggest that the MiniVector system is a promising delivery vector for in vivo gene targeting therapy.

The circular MiniVector, as described herein, is composed only of a transcription promoter (H1), designed sequences encoding therapeutic shRNA for a targeting gene, and integrase-mediated in vivo recombination sites (FIG. 1). Due to its—small size (in this example Minivectors are ~385 bp) the MiniVector can have more numbers of molecules for a given volume/mass and higher cell transfection efficiency than that of conventional DNA plasmid vectors. In addition, it is possible that the copy numbers of shRNA could be significantly amplified via repeated gene transcription from the H1 promoter within the transfected cells. In contrast, transfected synthetic siRNA cannot increase in copy numbers in cells. Synthetic siRNAs are also completely destroyed during RNA-interference mediated gene silencing and therefore require constant replenishment. In addition to monomeric forms of minivectors for gene silencing, polymer forms of minivectors can also be formed during in vivo recombination and can be purified using similar techniques. Such dimer/polymer forms of minivectors can be tested for their gene silencing potential using the techniques described herein. Moreover, it is possible to insert sequences encoding multiple therapeutic shRNAs and produce a MiniVector with simultaneous multi-gene targeting potential in the transfected cells, resulting in a highly sensitive and specific gene therapy.

Example 2

Minivector Encoding shRNA Blocks GFP Expression in Human Fibroblasts

Figure 4:
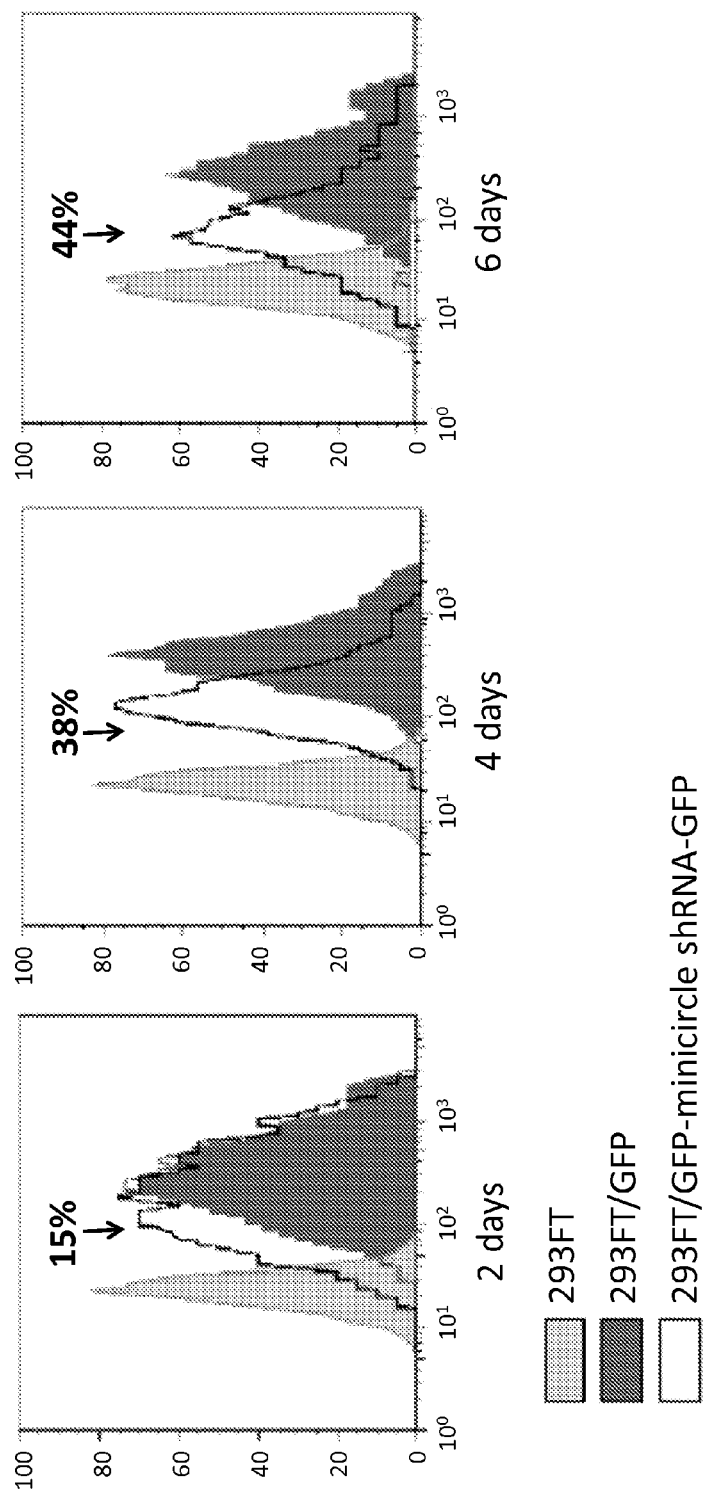
FIG. 4 shows silencing of GFP over time with MiniVector encoding shRNA against GFP. 293FT cells stably expressing GFP were transfected with MiniVector for three hours. Cells were collected at the indicated times following transfection and were submitted simultaneously to fluorescence microscopy (data not shown) and flow cytometry.
Figure 5:
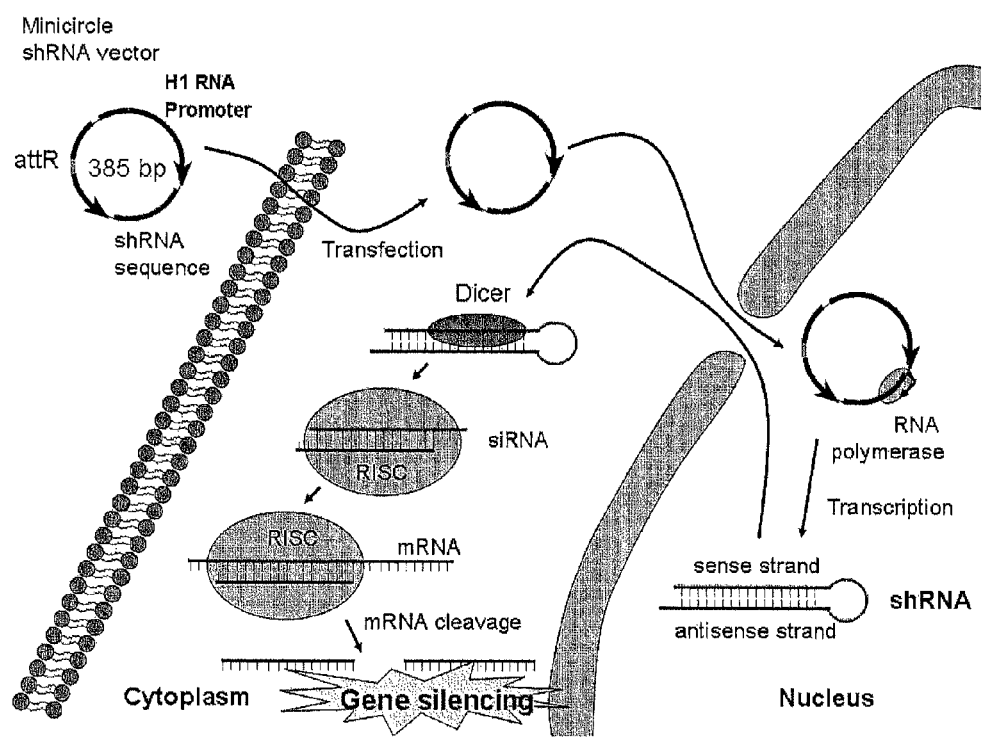
FIG. 5 shows a schematic of the MiniVector-directed gene knockdown. Supercoiled MiniVector contains the residual attR site from the method used to generate the minicircles (Fogg et al. 2006), the H1 RNA promoter, and a short hairpin RNA (shRNA). To regulate gene expression, the minicircle is taken up into the nucleus where human RNA polymerase (II or III) transcribes it into shRNA. The shRNA is exported to the cytoplasm where the enzyme Dicer processes it. Subsequently, the RISC complex displaces the sense strand and uses the remaining antisense strand of the siRNA to target an mRNA, leading to mRNA degradation and gene silencing. The shRNA can also encode miRNA to regulate classes of genes.

The transfection efficiency of MiniVectors encoding shRNA targeted to GFP (MiniVector shRNA-GFP) was assayed in human embryonic kidney cells that stably express GFP (293FT/GFP). Minivector encoding shRNA against CCR5, which is not found in 293FT cells, served as a negative control. Following transfection using Lipofectamine®, GFP expression was quantified using fluorescence activated cell sorting. Compared to cells transfected with the control MiniVector, which had no effect on GFP-mediated fluorescence, cells receiving MiniVector showed decreased fluorescence in a dose- and time-dependent manner with up to 44% decreased fluorescence (FIG. 4). Therefore, minivectors encoding shRNA against the GFP gene appear to be processed through the Dicer pathway as schematized in FIG. 5 to silence GFP expression.

Figure 6:
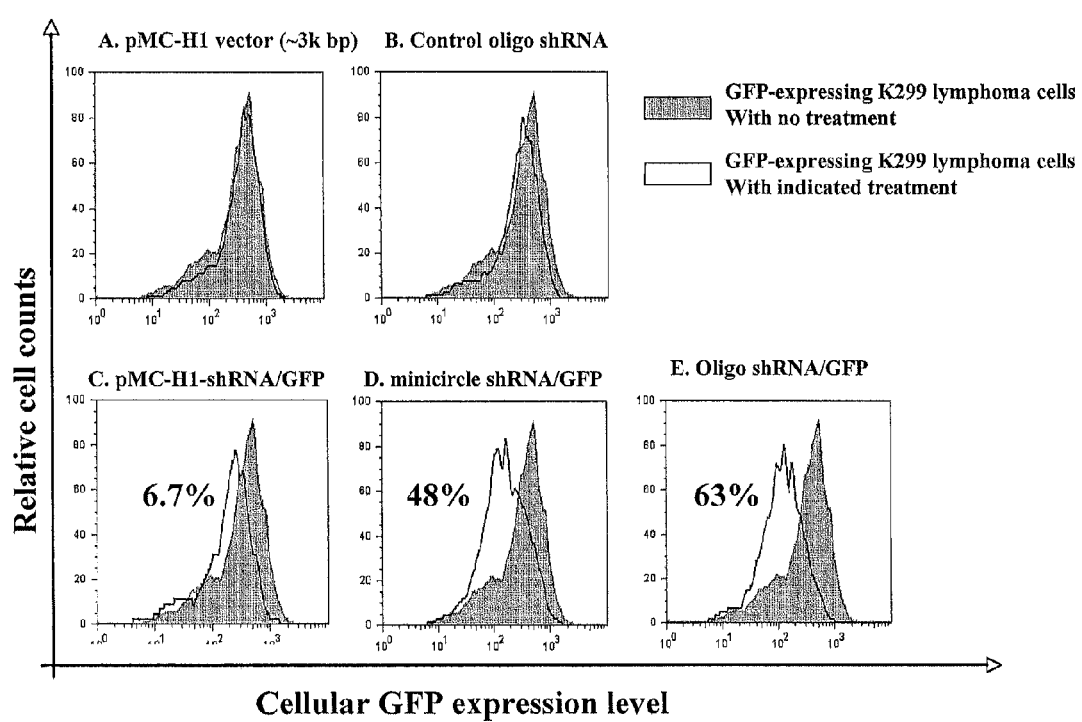
FIGS. 6A-E show vector comparison for silencing GFP in human lymphoma cells. Human Karpas 299 lymphoma cells stably expressing GFP were transfected using Lipofectamine 2000, with traditional plasmid vector (C), MiniVector (D), or synthesized shRNA (E) encoded to silence GFP. Cells were collected four days after transfection and were submitted to flow cytometry. Changes in GFP expression were compared between the treated cells (open peaks) and untreated cells (gray peaks). As controls, non-relevant shRNA (FIG. 6B) and pMC vector with no insert (FIG. 6A) were used.

Minivector encoding shRNA silences GFP expression in Jurkat lymphoma cells more effectively than a conventional shRNA plasmid vector. Human karpas 299 cells stably expressing GFP were generated. This cell line was used to compare the transfection and silencing efficiency of MiniVector and a conventional plasmid. The Minivector, mv-H1-GFPshRNA (FIG. 6D) was compared to a conventional plasmid vector encoding the same shRNA to GFP, pMV-H1-GFPshRNA (FIG. 6C). In addition, a synthetic siRNA was tested with the same sequences used in DNA vectors (FIG. 6E).

As shown in FIGS. 6A-B, control pMV-H1 vector and Minivector expressing a control shRNA had no effect on cellular GFP expression. Transfection of cells with conventional plasmid vector pMV-H1-GFPshRNA silenced GFP gene expression 6.7% of treated cells (FIG. 6C). However, MiniVector treatment silenced GFP in 48% of the treated cells (FIG. 6D), which is comparable to that induced by oligomeric shRNA, (61%) (FIG. 6E).

Example 3

Transfection of Human Dendritic and T Cells

Figure 7:
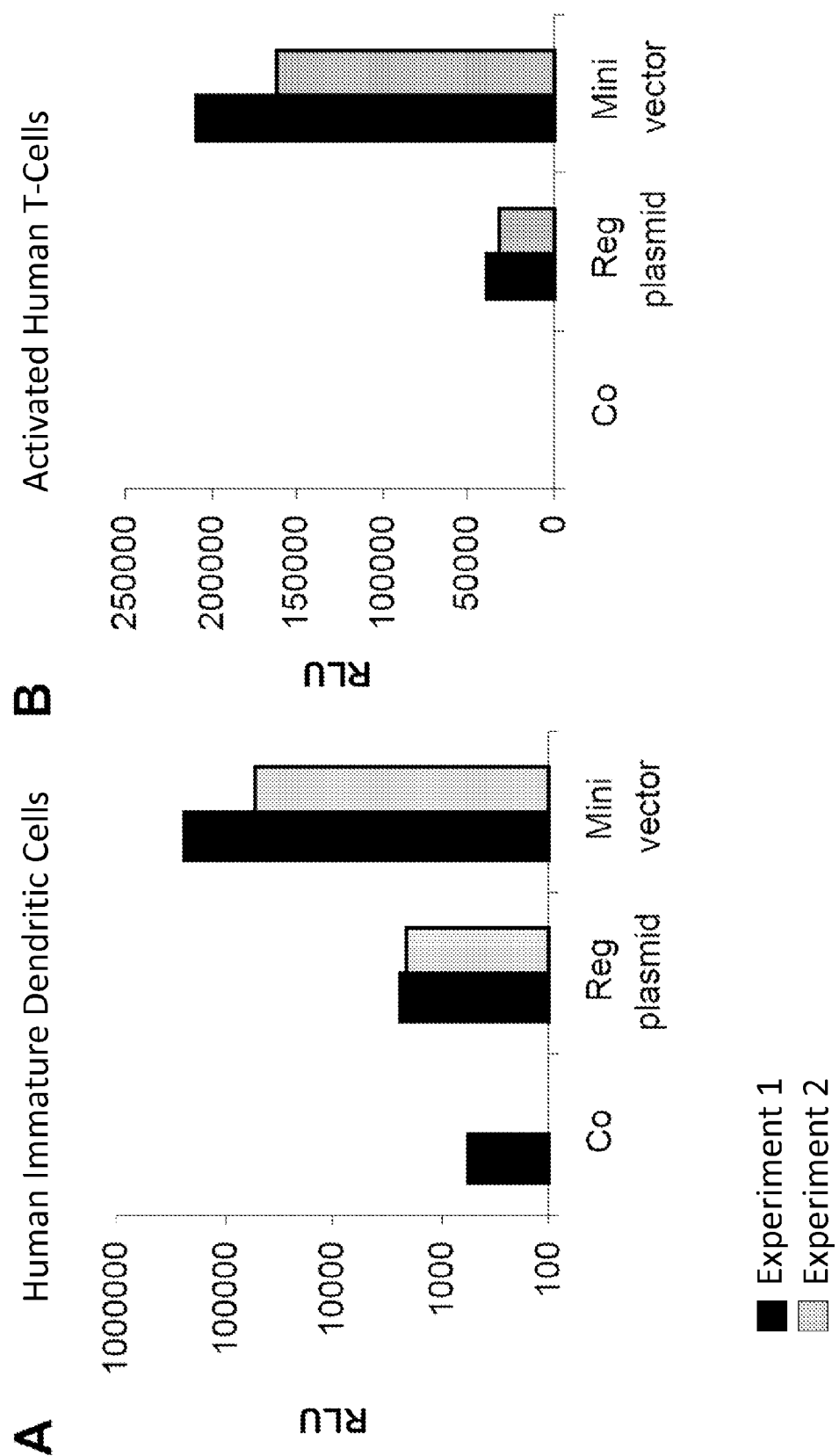
FIGS. 7A-B show that transfection of human dendritic cells (DCs) and T-cells with minivectors results in enhanced gene expression. Human immature DCs (FIG. 7A) or CD3/CD28-activated T-cells (FIG. 7B) were transfected with mock (Co), regular (Reg) plasmid, or MiniVector encoding Gaussia Luciferase (GLuc) using GeneJuice®. After transfection, maturation cocktail was added to the DCs. Luciferase activity in Random Light Units (RLU) was determined 48 h post transfection. There was higher gene expression in cells with minivectors compared to regular plasmid in two independent experiments (gray and black).

Minivector encoding Gaussia luciferase transfected human dendritic cells and activated T-cells with high efficiency. A system was established to measure the ability of activated T-cells to combat tumors (Ahmed et al. 2007, J. Immunother. 30(1):96-107). A short luciferase gene, Gaussia Luciferase, was cloned into the minivectors to make mvGLuc. Despite being one of the smallest easily trackable genes available, the luciferase gene resulted in relatively large minivectors ~1.2 kb, which are far larger than the ~385 bp MiniVectors used in the experiments that showed regulation of GFP expression above. The GLuc-encoding MiniVectors are, however, still smaller than typical DNA plasmid vectors and, importantly, lack any bacterial sequences for selection or replication. As shown, GLuc-delivery into human dendritic cells (DCs) (FIG. 7A) and T-cells (FIG. 7B) resulted in higher gene expression in comparison to the regular plasmid. These results show two significant things. First, minivectors can be used to deliver small genes that can be transcribed and translated into functional proteins. Second, and demonstrating the great promise of these vectors, the MiniVector can transfect DCs and T-cell lines in which non-viral transfection has had little to no success previously.

Example 4

Activity of Gaussia Luciferase in Mouse Lung 1,613 bp Minivectors encoding the non-secreted form of Gaussia Luciferase under the control of the CMV promoter or various controls were administered intranasally (5 µg) to out-bred female NIH Swiss mice. Half of the mice were given MiniVector in water (mcGLuc+H$_2$O) and the other half were given MiniVector in PEI (mcGluc+PEI). Control mice did not receive any DNA. After 72 hours post-administration of MiniVectors, mice were sacrificed and their lungs were harvested. Whole lungs were homogenized using beads and lysis buffer then assayed using an ELISA for luciferase activity.

MiniVectors both transfected murine lungs and expressed Gaussia Luciferase, even in the absence of PEI. These results are significant because it indicates that no transfection vehicle, which is usually toxic, may be needed during treatment. Additional experiments could include using other minivectors that express different proteins or shRNA to silence specific genes within the lung cells, as well as administering the minivectors by aerosolization using an Aerotech II nebulizer.

Example 5

Assessment of Shearing Forces on Minivectors

Materials and Methods
Chemicals, Reagents, and Equipment

All chemicals were purchased through Fisher Scientific (Waltham, Mass.), except for the acrylamide (EMD Chemicals, Merck KGaA, Darmstadt, Germany), agarose (ISC BioExpress, Kaysville, Utah), and SYBR® Gold (Invitrogen, Hercules, Calif.). All restriction enzymes were purchased from New England Biolabs (Ipswich, Mass.). Plasmid Maxi kit was from Qiagen (Valencia, Calif.) and Amicon Ultra centrifugal filters were from Millipore (Billerica, Mass.). The Aerotech II jet nebulizer was purchased from Pharmalucence (Bedford, Mass.) and the Aridyne 2000 compressor was from Allied Healthcare Products (St. Louis, Mo.). The ⅛" probe sonicator (Model 60 Sonic Dismembrator) is from Fisher Scientific (Waltham, Mass.). Software programs of PC Image and Total Lab were purchased from Fotodyne (Hartland, Wis.) and TotalLab (Durham, N.C.), respectively.

DNA Generation and Manipulation

A number of plasmids and MiniVectors, covering a wide range of sizes varying from 281 bp to 5,302 bp were subjected to shear forces generated through aerosolization through a Aerotech II nebulizer or to shear forces generated by sonication. Throughout the text, these vectors are referred to only by their length because that is the main variable being assessed. Following the convention of using "p" in front of plasmid names, MiniVector are designated with "mv". Parent plasmids used to generate Minivector are designated "pMV". Parent plasmids, pMV-KB4TAL-GLucKDEL and pMV-CMV-GLucKDEL, were gifts from Dr. David Spencer (Baylor College of Medicine), and pMV-KB4TAL-mCherry and pMV-CMV-mCherry were gifts from Dr. Martin Matzuk and Dr. Zhifeng Yu (Baylor College of Medicine). pQR499 was a gift from Dr. John Ward (University College London, U.K.). pDJC1 was constructed by digesting pQR499 with TfiI and AflIII. The recessed ends of the digested pQR499 were filled in with T4 DNA polymerase and subsequently ligated with T4 DNA ligase. Plasmids were generated in *E. coli* DH5α cells and were isolated using a Plasmid Maxi Kit as per manufacturer's instructions, and subsequently desalted and concentrated using Amicon Ultra centrifugal filters. MiniVector were obtained as follows. MiniVector parent plasmids were transformed into *E. coli* strain LZ54 (Zechiedrich et al. 1997) and large-scale λ Int-mediated recombination and Minivector isolation was performed as described (Fogg et al. 2006; Zhao et al. 2010). To generate nicked DNA vector, nicking endonuclease Nt.BbvCI was used following manufacturer's protocols. Linearization was performed with PvuI, BspHI, or ScaI as per manufacturer's protocols.

DNA Shearing

For nebulization, 10 mL of DNA at 1 ng$\mu$L$^{-1}$ in TE (10 mM Tris-HCl, 1 mM EDTA, pH 8) was added to an Aerotech II jet nebulizer. Air was delivered to the nebulizer at a rate of 10 L/min and gauge pressure of 50 p.s.i. by an Aridyne 2000 compressor. During nebulization, aerosol was captured using an all glass impinger (AGI) for 3 min at 0.5-3.5 min, 7-10 min, 20-23 min, and 25-28 min, in which the AGI reservoir held 20 mL TE. Aerosol output was approximately 0.3 mLmin$^{-1}$. Simultaneously, 15 µL samples were taken from the nebulizer reservoir.

For the remaining studies of the effects of DNA length on nebulization survival, 15 µL aliquots were removed from the nebulizer reservoir prior to and at intervals throughout nebulization up to 30 min at which point the DNA solution was depleted. Because of the dramatic changes that occurred early, aliquots were taken at one- or two-minute intervals, initially.

For sonication, 1 mL of DNA at 1 ng$\mu$L$^{-1}$ in TE in an eppendorf tube was incubated on ice during sonication with a ⅛" probe sonicator set at "5", which corresponds to a power output of 7 watts (Root Mean Square). 15 µL aliquots were removed prior to and during sonication at the timepoints indicated in the data. All DNA shearing experiments were performed a minimum of three separate times. DNA was analyzed by gel electrophoresis on 1% agarose gels for >1,000 bp or 5% acrylamide (29:1 acrylamide:bis-acrylamide) gels for DNA <1,000 bp in 40 mM Tris-acetate and 2 mM EDTA. All gels were submitted to 125 volts for 2 hours, stained with SYBR® Gold (Invitrogen, Hercules, Calif.) for 20 min and visualized using PC Image. Total Lab was utilized to quantify the remaining DNA.

Results

Effect of DNA Length on Resistance to Shear

There are multiple processes that generate hydrodynamic shear, including passage through a narrow gauge needle, circulation through a HPLC pump, nebulization, and sonication; these methods are routinely used to generate DNA fragments for sequencing or for shotgun cloning (Sambrook and Russell, Molecular Cloning: A Laboratory Manual, 2006). Nebulization was chosen first for its reproducibility and clinical relevance. In the cases where the DNA vectors resisted shear forces from nebulization, sonication was used because it can generate much higher shear forces for longer time frames than the nebulizer while maintaining reproducibility. To facilitate comparisons between different DNAs, the term, Survival$_{50}$, is used to indicate the time needed to degrade half of the DNA. The terms (Neb) and (Son) in parenthesis refer to nebulization and sonication respectively. The Survival$_{50}$ values for each DNA, obtained as described below, are also listed in Table 1.

DNA samples were subjected to nebulization in a Collison-like jet nebulizer (May K. R. (1973) The Collison Nebulizer. Description, Performance & Application J. of Aerosol Science, Vol. 4, #3, p. 235). The nebulizer works as follows: high-pressured air is pumped through a small orifice in the nozzle. The pressure differential between the nozzle and reservoir siphons the therapeutic solution from the reservoir into the high velocity jetstream thus generating primary droplets 15 to 500 nm in size (Lentz et al. 2005, Aerosol Science 36, 973-990). Minimal DNA degradation occurs during this primary droplet formation (Lentz et al. 2005, Aerosol Science 36, 973-990); however, the droplets are too large to penetrate deep into the lungs (Eberl et al. 2001, Eur J Nucl Med. 2001 September; 28(9):1365-72). A plastic cone within the baffle breaks the primary droplets into smaller (1-10 nm) ones that can penetrate deep into the lungs (Bennet et al. 2002, Journal of Aerosol Medicine, 15, 179-188). DNA shearing occurs almost exclusively during impact with the plastic cone within the baffle (Lentz et al. 2005, Aerosol Science 36, 973-990).

The smaller droplets that escape the baffle area exits the nebulizer in aerosol form. A removable lid allows for sampling from the reservoir.

Only a small fraction of the small droplets are carried out the mouthpiece with the air-flow; the majority of the droplets condense back into the reservoir where they are recirculated through the nozzle. As a consequence, the DNA in the reservoir becomes increasingly sheared over time.

Because of the rapidity of the condensation and aerosolization, the state of the DNA in the reservoir is identical to that in the aerosol (Knight et al., 1988, J of Infect Diseases, 158(2): 443-8). It is easier and less complicated to collect samples from the reservoir than to capture the aerosol, so samples from the aerosol and the reservoir were compared (data not shown). DNA degradation was identical from both sites for DNAs representing both ends of the length spectrum tested in this study, a 3,869 bp plasmid or a 385 bp MiniVector. In the remaining nebulization experiments, therefore, samples were drawn from the reservoir.

Figure 8B:
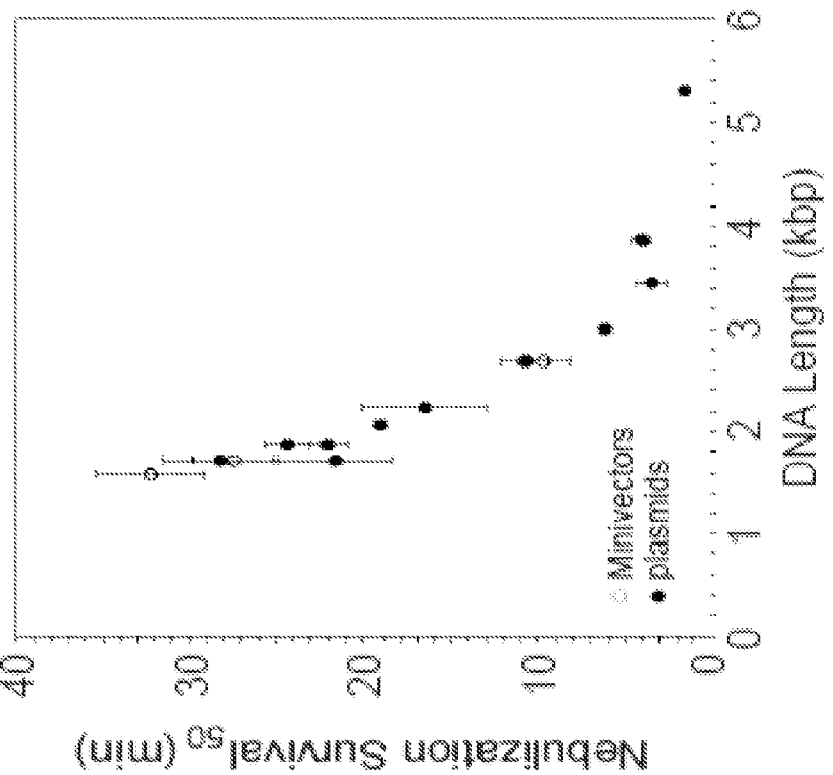
FIGS. 8A-B are graphical representations summarizing DNA shearing as a function of length (averaged for at least three separate experiments).
Figure 8A:
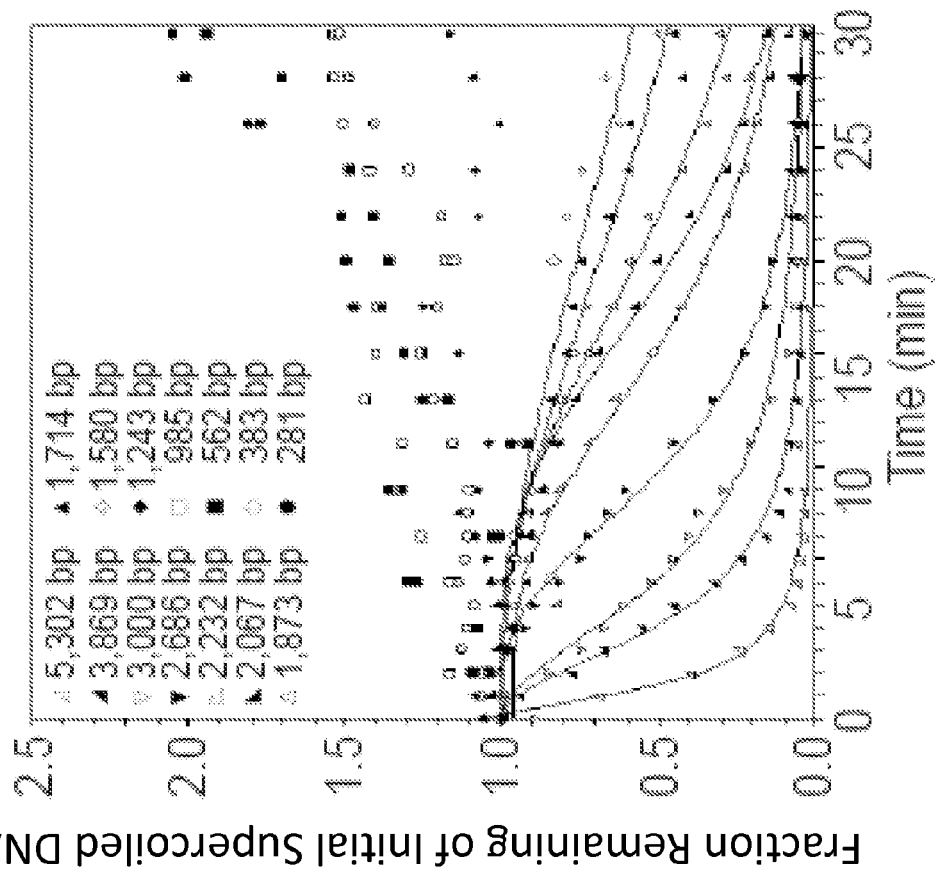

Supercoiled DNAs varying from 281 to 5,302 bp were subjected to nebulization and their survival was quantified by gel electrophoresis. The extent of DNA shearing was determined from the disappearance of full-length (intact) DNA vector over time. The results were highly reproducible and independent of the DNA concentration. DNA concentrations ranging from 1 µg/ml to 10 µg/ml gave identical results for DNA of 1,873 bp (data not shown). The relationship between DNA length and shearing was strongly proportional. In addition, DNAs decayed differently depending upon length (FIGS. 8A-B). Supercoiled DNA >2,600 bp fragmented rapidly and displayed pseudo-exponential decay. Supercoiled DNA vectors between 1,580 and 2,232 bp exhibited an initial resistance to shearing, as can be seen by the sigmoidal shaped curves in FIG. 8A-B, and then degraded. Supercoiled Minivector $\leq$1,243 bp did not decay measurably, and exhibited a slight concentrating effect with time due to evaporation of the aqueous solvent.

A relatively large MiniVector, pMV-CMV-Luc2 (2,679 bp) had a relatively short survival time in the nebulizer, comparable to a similar sized plasmid, indicating that the difference in shear survival times between plasmids and Minivector is not because of differences in sequence (e.g., origin of replication, gene encoding antibiotic resistance on the plasmid).

The concentration effect during nebulization has been observed previously with small drugs that are resistant to shearing. This concentrating effect becomes more pronounced toward the end of the nebulization when the reservoir volumes are small. DNA >3,000 bp is completely sheared during the early part of the nebulization. Therefore, the concentration effect was negligible for quantifying the shearing of these large DNA vectors, but the concentration effect posed a challenge for data quantification for DNA $\leq$1,243 bp.

Although supercoiled Minivector of 1,243-1,714 bp were largely intact following nebulization, sheared fragments were visible as a smear of shorter DNA fragments running ahead of the supercoiled band (data not shown). The typical degradation length of these fragments from plasmids and these larger MiniVectors was between 200-1,000 bp.

Because there was no detectable shearing of 385 bp MiniVector in the nebulizer, the resistance of this Minivector to shear forces generated by sonication was tested; Survival50 (Son) for DNA vectors <1,243 bp was then measured. The Survival$_{50}$(Son) of the 999 bp vector was 28 min. In comparison the Survival$_{50}$(Son) of a 3,869 bp plasmid during sonication under identical conditions was only 0.37 min, demonstrating the much higher shear-resistance of the MiniVector relative to a conventional plasmid vector.

Effect of DNA Topology on Resistance to Shear Forces

Linear, nicked and relaxed forms of the 1,873 bp pQR499 plasmid and 999 bp MiniVector were generated to investigate the effect of DNA topology on resistance to shear forces. These topological forms of DNA were subjected to either nebulization (for the 1,873 bp) or sonication (for the 999 bp) and their survival was quantified with time (FIG. 9). As expected, DNA supercoiling had a strong protective effect on shear force survival. The Survival$_{50}$(Neb) for the 1,873 bp DNA in its linear form was ~4 min, compared to ~22 min in its negative supercoiled form. Thus, without the benefit of supercoiling-mediated compaction, linear DNA likely has a much larger hydrodynamic diameter; linearized 1,873 bp DNA was sheared similarly to that of a much larger (>3,000 bp) supercoiled DNA plasmid. Nicked (open-circle) DNA lasted ~4-fold longer than linear, reflecting how circularity reduces the hydrodynamic diameter. One might predict that a preexisting nick would reduce DNA vector survival. Relaxed 1,873 bp (with both strands covalently closed) survived the same as the nicked 1,873 bp plasmid. Thus, a nick does not further subject DNA to shear force. As the nicked, relaxed, or supercoiled DNA was sheared by nebulization, we never observed any degradation products corresponding to the full-length linear form. This is most likely a consequence of the short lifetime of linear DNA, as soon as full length linear forms it will rapidly shear and therefore will not accumulate. Negatively supercoiling provided a reproducible improvement in shear survival (~1.3 fold) over nicked and relaxed 1,873 bp DNA.

A similar dependence on DNA topology was observed for the 999 bp MiniVector. Linear 999 bp DNA was rapidly degraded during sonication. Nicked 999 bp DNA survived about 7-fold longer than linear. Supercoiled 385 bp MiniVector lasted about 4-fold longer than nicked 999 bp DNA, which was a more dramatic improvement than was observed for supercoiled 1,873 bp DNA.

Discussion

MiniVector less than 2,000 bp are not significantly degraded in a nebulizer. Resistance of Minivectors to shear forces appears to be mostly attributable to its small size. Survival time in the nebulizer increases sharply as the plasmid size drops below 3,000 bp (FIG. 9).

Efforts to Protect DNA from Shear Forces

Much effort has been and continues to be put forth in improving the composition of the vehicle systems to protect fragile traditional plasmid DNA vectors or siRNA during delivery. Cationic agents, such as polyethylenimine (PEI), condense the DNA, reducing the hydrodynamic diameter, thereby helping to protect the DNA from shearing (Belur et al. 2007, Nat Protoc 2: 146-52, and Lentz et al. 2005, Aerosol Science 36, 973-990). Most of these vehicles are, unfortunately, cytotoxic (Brunot et al. 2007. Biomaterials 28:632-40; Moghimi et al. 2005, Molecular therapy 11: 990-5), limiting their utility. PEI is cytotoxic when delivered to the blood, but is less toxic when delivered by aerosol as compared to systemic administration (Di Giola and Conese, 2009, Drug Des Devel Ther. 2009 Feb. 6; 2:163-88). The ability of Minivectors to resist the shear forces associated with delivery, even in the absence of condensing agents should reduce the need for toxic vehicle. Some vehicle will presumably still be needed for the DNA to be able to enter into cells in the lung, although this should be less than would be required for a conventional plasmid DNA vector.

Therapeutic Consequences on Gene Therapy of DNA Shearing

The obvious detriment of DNA shearing is a reduction in the amount of intact, biologically active vector remaining for therapy. It could be argued that the dose of DNA delivered could simply be increased to compensate for the loss of supercoiled vector. Doing this would have two negative consequences. First, increasing the amount of vector requires a commensurate increase in the amount of cytotoxic delivery vehicle. Second, large plasmid DNA is broken into shorter linear DNA fragments. Vector associated toxicity may result from the delivery of short linear DNA fragments. Additional outcomes of delivering sheared DNA include DNA degradation, and induction of DNA repair and recombination pathways, potentially resulting in genome instability. Free DNA ends are quickly processed in the cell. On one extreme, DNA ends could trigger apoptosis, especially if delivered in large quantities. On the other extreme, the cell could repair and ligate the DNA in a random fashion to form large episomal concatemers. This has been reported for linear DNA delivered to mouse livers and in that case, resulted in stable long-term transgene expression that persists for several weeks (Chen et al., 2001, Molecular Therapy, 3, 403-410). It is possible that the random DNA fragments resulting from DNA shearing would join together to generate new sequences, with the potential for new toxic gene products.

It is important, therefore, that Minivectors did not merely survive nebulization and sonication for longer than traditional plasmid vectors during nebulization but survived intact with very little if any DNA degradation. Therefore, the risk of delivering short linear DNA fragments is reduced considerably by using smaller, supercoiled DNA vectors.

Model for DNA Shearing

DNA supercoiling may have conflicting effects on shear survival. The torsional strain in supercoiled DNA might make the molecule more susceptible to shearing, whereas compaction increases shear resistance (Lengsfeld and Anchordoquy, 2002, Journal of Pharmaceutical Sciences, 91, 1581-1589). The data herein show that the beneficial effect of compaction is the dominant effect. The advantage provided by supercoiling decreases as the DNA becomes larger.

DNA Vector Delivery to the Lungs

Identifying DNA vector lengths that survive shear forces has important implications for gene therapy delivery no matter what the delivery route; however, the use of a Collison-like jet nebulizer makes our data particularly germane for therapeutic delivery to the lungs. The lungs are readily accessible by intravenous, intratracheal, intranasal and aerosol delivery methods), and any of these routes is amenable to DNA vector delivery. However, delivery of nucleic acids by aerosol is noninvasive, delivers directly to the affected tissue, and may help prevent complications in non-target organs. Additionally, aerosol delivery allows DNA to be delivered to the lungs in much higher quantities than may be obtained by systemic administration (Bennet et al. 2002, Journal of Aerosol Medicine, 15, 179-188). A number of promising gene therapy targets have been identified for the treatment of pulmonary diseases. Dozens of gene therapy clinical trials are ongoing that target cystic fibrosis treatment; disappointingly, however, the therapy has so far been unsuccessful (O'Sullivan and Freedman, 2009, Lancet, 373, 1891-1904). Asthma also has high potential as a disease target for RNA interference (Duncan et al., 2008, Molecular Pharmaceutics, 5, 559-566) shRNA (Kozma et al., 2006, J. Immunol. 176: 819-26) or microRNA (miRNA).

Example 6

Attachment of Chemical Moieties to Supercoiled MiniVectors

Figure 10:
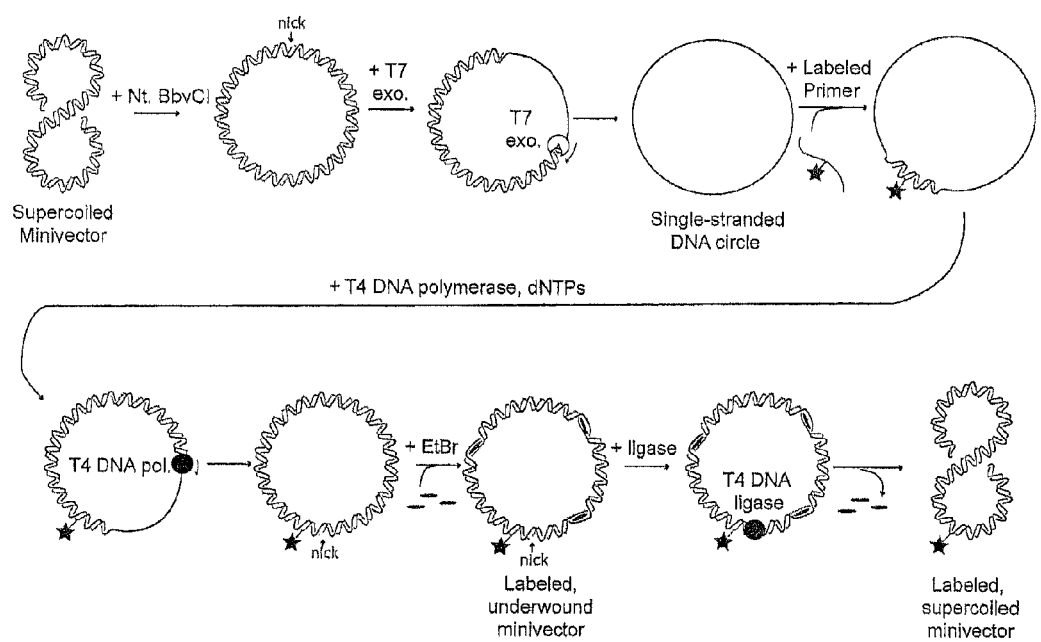
FIG. 10 depicts the process for attachment of chemical moieties to supercoiled minivectors.

A single-stranded circular DNA template was generated by first nicking supercoiled MiniVector with a nicking endonuclease, Nt. BbvCI. T7 exonuclease was then able to initiate nucleotide removal at the nick until the strand that was nicked was completely digested. The intact strand lacked a 5' terminus for the exonuclease to act upon and therefore remained undigested. An internally labeled, 5' phosphorylated, oligonucleotide primer was then annealed to the circular ssDNA template. The second strand was subsequently resynthesized using T4 DNA polymerase, starting and finishing at the primer, resulting in nicked, circular, labeled DNA. To restore supercoiling, ethidium bromide (EtBr), an intercalator that partially unwinds the DNA helix, was added. Sealing of the nick by T4 DNA ligase trapped the unwinding. Subsequent removal of the EtBr by butanol extraction produced negatively supercoiled, labeled MiniVector. A flow diagram of the process is shown in FIG. 10.

Products at various stages of the procedure were analyzed by polyacrylamide gel electrophoresis on a 5% polyacrylamide gel. DNA was visualized by staining with SYBR Gold or visualized by excitation with a 532 nm laser using a Typhoon Imager (GE Life Sciences) to detect for the presence of the fluorescent Cy3 label. Cy3 fluorescence is only detected in latter stages of the procedure, following the annealing of the labeled primer and resynthesis of the second strand.

Cy3-labeled, 339 bp MiniVector was transfected into HeLa cells via liposomal transfectional reagent "Lipofectamine 2000®" after being purified through a 50K MW cutoff exclusion filter column to remove labeling primer unassociated with complete MiniVector. The same 339 bp MiniVector, lacking a fluorescent label, was transfected into HeLa in a parallel experiment as a negative control. Images three hours post transfection showed DAPI stained nuclei identified via the blue emission channel at 457 nm. Cy3 labeled DNA was identified via the near red emission channel at 617 nm. Images confirmed the presence of the Cy3 labeled DNA and the ability to visualize Minivector DNA via fluorescence imaging methods (data not shown).

References

1. Taroncher-Oldenburg G, Marshall A. Trends in biotech literature 2006. *Nature biotechnology* 2007; 25(9): 961.
2. Kurreck J. RNA interference: from basic research to therapeutic applications. *Angewandte Chemie (International ed* 2009; 48(8): 1378-98.
3. Kim B, Tang Q, Biswas P S, Xu J, Schiffelers R M, Xie F Y et al. Inhibition of ocular angiogenesis by siRNA targeting vascular endothelial growth factor pathway genes: therapeutic strategy for herpetic stromal keratitis. *The American journal of pathology* 2004; 165(6): 2177-85.
4. Haussecker D, Cao D, Huang Y, Parameswaran P, Fire A Z, Kay M A. Capped small RNAs and MOV10 in human hepatitis delta virus replication. *Nature structural & molecular biology* 2008; 15(7): 714-21.
5. Shi Y. Mammalian RNAi for the masses. *Trends Genet.* 2003; 19(1): 9-12.
6. Brummelkamp T R, Bernards R, Agami R. A system for stable expression of short interfering RNAs in mammalian cells. *Science* (New York, N.Y. 2002; 296(5567): 550-3.

7. Ma H T, On K F, Tsang Y H, Poon R Y. An inducible system for expression and validation of the specificity of short hairpin RNA in mammalian cells. *Nucleic acids research* 2007; 35(4): e22.
8. Darquet A M, Cameron B, Wils P, Scherman D, Crouzet J. A new DNA vehicle for nonviral gene delivery: supercoiled MiniVector. *Gene therapy* 1997; 4(12): 1341-9.
9. Yew N S, Zhao H, Przybylska M, Wu I H, Tousignant J D, Scheule R K et al. CpG-depleted plasmid DNA vectors with enhanced safety and long-term gene expression in vivo. *Mol Ther* 2002; 5(6): 731-8.
10. Reyes-Sandoval A, Ertl H C. CpG methylation of a plasmid vector results in extended transgene product expression by circumventing induction of immune responses. *Mol Ther* 2004; 9(2): 249-61.
11. Ritter U, Damm-Welk C, Fuchs U, Bohle R M, Borkhardt A, Woessmann W. Design and evaluation of chemically synthesized siRNA targeting the NPM-ALK fusion site in anaplastic large cell lymphoma (ALCL). *Oligonucleotides* 2003; 13(5): 365-73.
12. Tiscornia G, Singer O, Ikawa M, Verma I M. A general method for gene knockdown in mice by using lentiviral vectors expressing small interfering RNA. *Proceedings of the National Academy of Sciences of the United States of America* 2003; 100(4): 1844-8.
13. Fogg J M, Kolmakova N, Rees I, Magonov S, Hansma H, Perona J J et al. Exploring writhe in supercoiled MiniVector DNA. *J Phys Condens Matter* 2006; 18(14): S145-S159.
14. Chen et al. (2004). Gene Therapy vol. 11, 856-864.
15. Li et al. 2006 *Proc. Natl. Acad. Sci.* vol. 103, 17337-17342.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

---

What is claimed is:

1. A nucleic acid molecule composition comprising a MiniVector, encoding a nucleic acid sequence, wherein said MiniVector lacks both a bacterial origin of replication and an antibiotic selection gene and wherein the MiniVector has a size up to about 2,500 base pairs.

2. The composition of claim 1, wherein the nucleic acid sequence comprises short hairpin RNA (shRNA) or micro RNA (miRNA).

3. The composition of claim 1, wherein the nucleic acid sequence comprises DNA that can be bound by a component selected from the group consisting of: a protein; a different DNA sequence; an RNA sequence; and a cell membrane.

4. The composition of claim 1, wherein the nucleic acid sequence comprises a gene.

5. The composition of claim 1, wherein the MiniVector comprises a chemical moiety, a modified oligonucleotide, and/or a modified backbone.

6. The composition of claim 5, wherein the chemical moiety is selected from the group consisting of: fluorescein, biotin, a dye, and cholesterol.

7. A mammalian, eukaryotic, or plant cell comprising the composition of claim 1.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
cacuuaguag uguaccgcct t                                              21

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
ggcgguacac uacuaagugt t                                              21

<210> SEQ ID NO 3
<211> LENGTH: 62
<212> TYPE: DNA
<213> ORGANISM: Artificial Sequence
<220> FEATURE:
<223> OTHER INFORMATION: Primer

<400> SEQUENCE: 3
gatccccgca agctgaccct gaagttcttc aagagagaac ttcagggtca gcttgctttt    60
ta                                                                   62

<210> SEQ ID NO 4
<211> LENGTH: 72
<212> TYPE: DNA
<213> ORGANISM: Artificial Sequence
```

```
<220> FEATURE:
<223> OTHER INFORMATION: Primer

<400> SEQUENCE: 4
gatccccgag ttggtcattg cgaggatgcc atttcaagag aatggtatcc tcgtaatgac    60
cagctctttt ta                                                       72
```